United States Patent [19]

Scott

[11] 4,234,315
[45] Nov. 18, 1980

[54] GAS CHROMATOGRAPHIC ANALYSIS METHOD AND APPARATUS

[75] Inventor: Richard L. Scott, Bartlesville, Okla.

[73] Assignee: Phillips Petroleum Company, Bartlesville, Okla.

[21] Appl. No.: 947,231

[22] Filed: Sep. 29, 1978

Related U.S. Application Data

[63] Continuation-in-part of Ser. No. 779,411, Mar. 18, 1977, abandoned, and Ser. No. 735,359, Oct. 26, 1976, abandoned.

[51] Int. Cl.$^3$ .................. G01N 31/08; G01N 31/12
[52] U.S. Cl. .......................... 23/230 PC; 23/232 C; 422/78; 422/89
[58] Field of Search ............... 23/230 PC, 232 C; 422/78, 89; 55/67, 386, 197; 73/23.1

[56] References Cited

U.S. PATENT DOCUMENTS

| | | | |
|---|---|---|---|
| 3,141,323 | 7/1964 | Taylor et al. | 55/67 X |
| 3,304,159 | 2/1967 | Hinsvark | 23/230 PC |
| 3,385,101 | 5/1968 | Roof | 23/232 UX |
| 3,425,807 | 2/1969 | Levy | 55/67 X |
| 3,428,432 | 2/1969 | Staunton et al. | 23/230 PC X |
| 3,518,059 | 6/1970 | Levy | 23/253 PC |
| 3,756,781 | 9/1973 | Kimbell | 23/230 PC |
| 3,838,969 | 10/1974 | Dugan | 23/230 PC |
| 3,992,175 | 11/1976 | Klementi et al. | 55/67 |

OTHER PUBLICATIONS

General College Chemistry, Richardson and Scarlett, Henry Holt Co., New York, 1940, p. 375.

*Primary Examiner*—R. E. Serwin

[57] ABSTRACT

A quantitative analysis system is provided wherein a sample is decomposed in a decomposition chamber, the reaction product mixture is passed to a first chromatographic zone wherein a first separation of the reaction mixture is carried out, the last major component eluting from the first chromatographic zone is measured and then vented, the first major components eluting from the first chromatographic zone are passed to a second chromatographic zone and the products eluting therefrom are measured. Alternatively, the first major component eluting from the second chromatographic zone can be passed to a third chromatographic zone for greater resolution, followed by measurement thereof, in which case the second major component eluting from the second chromatographic zone is vented.

A method is provided for the analysis for C, H and N by gas chromatography. A method is also provided for the analysis for oxygen, alone, and for oxygen and sulfur by gas chromatography.

116 Claims, 10 Drawing Figures

GAS CHROMATOGRAPHIC ANALYSIS METHOD
FOR ELEMENTAL OXYGEN AND SULFUR

—— COLUMN 1
---- COLUMN 2
—— COLUMN 3

GAS CHROMATOGRAPHIC ANALYSIS METHOD AND APPARATUS

This is a continuation-in-part of copending application Ser. No. 779,411, filed Mar. 18, 1977, now abandoned, which is a continuation-in-part of application Ser. No. 735,359, filed Oct. 26, 1976, now abandoned.

This invention relates to chromatography. In one aspect, this invention relates to the analysis for C, H and N by gas chromatography. In another aspect, this invention relates to the analysis for oxygen by gas chromatography. In yet another aspect, this invention relates to the analysis for sulfur by gas chromatography.

In the art of qualitative and quantitative identification of materials there exist many relatively elaborate and sophisticated methods of determining the composition of compounds and compositions. These methods include, among others, the measurement of volume or mass by chemical or physical techniques. Needless to say, many of these methods are costly and time consuming. Additionally, these methods often require the employment of highly skilled technicians for obtaining reliable data.

Carbon-hydrogen-nitrogen analyzers are noteably elaborate and, in general, slow and expensive. Conventionally, combustion-pyrolysis techniques for carbon, hydrogen and nitrogen depend upon quantitative conversions of these elements to specific, measureable molecules. Unfortunately, on many instruments it is impossible to be reasonably sure that such conversions are complete. For example, incomplete combustion of the carbon in a sample will give a low value for carbon dioxide. Additionally, the unconverted or partially converted products such as carbon monoxide and methane can appear together with the nitrogen peak, thus giving a high value for nitrogen. Further, other elements, such as sulfur and the halides, are often present in the sample. These elements are conventionally retained in the combustion tube; however, they do break through and can interfere with measurement of the desired products.

I have discovered that the problems inherent in the prior art techniques and apparatus for elemental analysis by gas chromatography are overcome by venting the major reaction products following their separation and detection.

Accordingly, it is an object of this invention to provide an improved method for determining the quantity and quality of the ingredients of a sample.

Another object is to provide an improved apparatus for gas chromatography.

Other objects, aspects and advantages of the present invention will be apparent to those skilled in the art from a reading of the following detailed description, appended claims and attached drawings.

In accordance with one aspect of the present invention there is provided a method for determining at least the elemental carbon, hydrogen and nitrogen contents of a sample which comprises the steps of subjecting the sample to be analyzed to complete combustion (or pyrolysis in appropriate cases), under selected reaction conditions, in a combustion (or pyrolysis) zone; passing carrier gas through the combustion zone, preferably after combustion is complete, to sweep the combustion products therefrom directly into a chromatographic separation zone where the combustion products are separated; and thereafter passing the separated products to a detection zone wherein the separated products are evaluated.

More spcifically, the sample to be analyzed is introduced into a closed, heated combustion chamber, oxygen or an oxygen source is introduced in the chamber and the sample is oxidatively decomposed under conditions whereby the resulting product mixture contains as its principal components carbon dioxide, water and nitrogen. The reaction product mixture is retained in the combustion chamber until combustion of the sample is substantially complete. A carrier gas, such as helium or argon, is then introduced to sweep the reaction product mixture into a first gas chromatographic column whereby the mixture is separated into its carbon dioxide, water and nitrogen component. The water normally elutes last from this first column. The effluent from the first column is then passed through a first detecting means to determine a property of the fluid mixture directed thereto which is representative of its composition.

The carbon dioxide and the nitrogen eluting from the first detector means are passed into a second gas chromatographic column whereby the nitrogen and carbon dioxide are further separated. The water eluting from the first detector means is vented. The effluent from the second chromatographic column is passed through a second detector means. The quantities of elemental hydrogen, carbon and nitrogen are then calculated from the quantities of water, carbon dioxide and nitrogen.

In one embodiment of the present invention, the nitrogen eluting from the second dector means is passed to a third chromatographic column whereby the nitrogen is further separated from other light gases which may be present. The carbon dioxide eluting from the second detector means is vented. The effluent from the third chromatographic column is passed through a third detector means.

In another embodiment of the present invention the nitrogen eluting from the first detecting means is passed to a second chromatographic column and the carbon dioxide eluting from the first detecting means is separately passed to a third chromatographic column. The effluents from the second and third columns are passed to second and third detecting means, respectively.

The following list illustrates the form in which the titled elements can be expected to be found:

1. Carbon-containing peaks: $CO_2$, $CO$, $CH_4$, $HCN$ and $COS$.
2. Hydrogen-containing peaks: $H_2$, $H_2O$, $CH_4$, $NH_3$, $HCl$, $HBr$, $HCN$ and $H_2S$.
3. Nitrogen-containing peaks: $N_2$, $N_2O$, $NO$, $NO_2$, $NH_3$ and $HCN$.
4. Sulfur-containing peaks: $SO_2$, $SO_3$, $COS$ and $H_2S$.
5. Halide-containing peaks: $HCl$, $Cl_2$, $HBr$ and $Br_2$.
6. Oxygen-containing peaks (decomposed in the absence of oxygen): $O_2$, $CO$, $CO_2$, $SO_2$, $SO_3$, $CO_3$, $NO$, $N_2O$ and $NO_2$.

Most of these peaks will be small as compared to carbon dioxide, water, nitrogen, sulfur dioxide, hydrogen chloride and hydrogen bromide. It is, however, desirable that a quantitative analysis of a sample include all of the above forms.

In accordance with another aspect of this invention there is provided a method for determining at least the oxygen content of a sample which comprises subjecting the sample to be analyzed to complete pyrolysis, in the absence of added oxygen, under selected reaction conditions, in a pyrolysis zone; passing a carrier gas through the pyrolysis zone to sweep the pyrolysis products therefrom through a bed of carbon and, optionally, platinum gauze, then into a chromatographic separation zone where the pyrolysis products are separated; and thereafter passing the separated products to a detection zone wherein the separated products are evaluated.

More specifically, the sample to be analyzed is introduced into a heated, closed pyrolysis chamber and the sample is decomposed under conditions whereby the resulting product mixture comprises carbon dioxide, carbon monoxide and water. The reaction product mixture is retained in the pyrolysis chamber until pyrolysis of the sample is substantially complete. A carrier gas, such as helium or argon, is then introduced to sweep the reaction mixture through the carbon bed. When the carbon dioxide and water are contacted with carbon at a high temperature, generally above 1100° C., they are converted to carbon monoxide and hydrogen, as shown by the following general equations:

$$C + CO_2 \rightarrow 2CO$$

$$C + H_2O \rightarrow CO + H_2$$

Optionally, the reaction mixture is then passed through hot platinum gauze to crack any long chain hydrocarbon pyrolyzates or unconverted hydrocarbons.

The carbon and the platinum gauze can be present in the pyrolysis chamber, preferably, at or near the outlet thereof.

Following contact with the carbon, and optionally with the platinum gauze, the reaction mixture is passed into a first chromatographic column whereby a first separation of the mixture is effected. The major oxygen-containing component of the reaction mixture is carbon monoxide, although some unconverted water and/or carbon dioxide may also be present. The water normally elutes last from this first column. The effluent from the first column is then passed through a first detecting means to determine a property of the fluid mixture directed thereto which is representative of its composition.

The carbon monoxide eluting from the first detector means is passed to a second gas chromatographic column wherein the carbon monoxide is further separated from other light gases which may be present. The water eluting from the first detector means is vented. Carbon dioxide, is present, can be separated on the first column, then vented with the water, or passed to a third chromatographic column as described previously. The effluent from the second column is passed through a second detector means. The quantity of elemental oxygen is then calculated from the quantities of carbon monoxide, carbon dioxide and water.

In accordance with yet another aspect of the present invention, there is provided a method for determining at least the sulfur content of a sample which comprises subjecting the sample to be analyzed to complete pyrolysis, in the absence of added oxygen, under selected reaction conditions, in a pyrolysis zone; passing hydrogen through the pyroiysis zone to sweep the pyrolysis products therefrom through a bed of carbon, then into a chromatographic separation zone where the pyrolysis products are separated; and thereafter passing the separated products to a detection zone wherein the separated products are evaluated.

More specifically, the sample to be analyzed is introduced into a closed, heated pyrolysis chamber and the sample is decomposed under conditions whereby the resulting product mixture comprises carbon monoxide, carbon dioxide, water and sulfur oxides. The reaction product mixture is reatined in the pyrolysis chamber until pyrolysis of the sample is substantially complete. Hydrogen is then introduced to sweep the reaction mixture through the carbon bed. The carbon dioxide and water are converted to carbon monoxide and hydrogen, as shown above. The sulfur oxides and hydrogen are converted to hydrogen sulfide and carbon monoxide, as shown, for example, by the following equation:

$$SO_2 + H_2 + C \rightarrow 2CO + H_2S$$

The carbon bed can be present in the pyrolysis chamber, as above.

Following contact with the carbon, the reaction mixture is passed to a first chromatographic column whereby a first separation of the mixture is effected. Hydrogen sulfide and any unconverted water are separated on the first column. The lighter gases, including carbon monoxide and unconverted carbon dioxide, are passed to a second chromatographic column. The water and hydrogen sulfide eluting from the first column are measured in a first detector means and then vented. The effluent from the second column is passed through a second detector means. The quantity of elemental sulfur is calculated from the quantity of hydrogen sulfide. Optionally, the quantity of elemental oxygen can be calculated from the quantities of carbon monoxide, carbon dioxide and water.

A better understanding of the method of this invention and a description of the apparatus will be had by reference to the drawings, of which:

Figure 1:
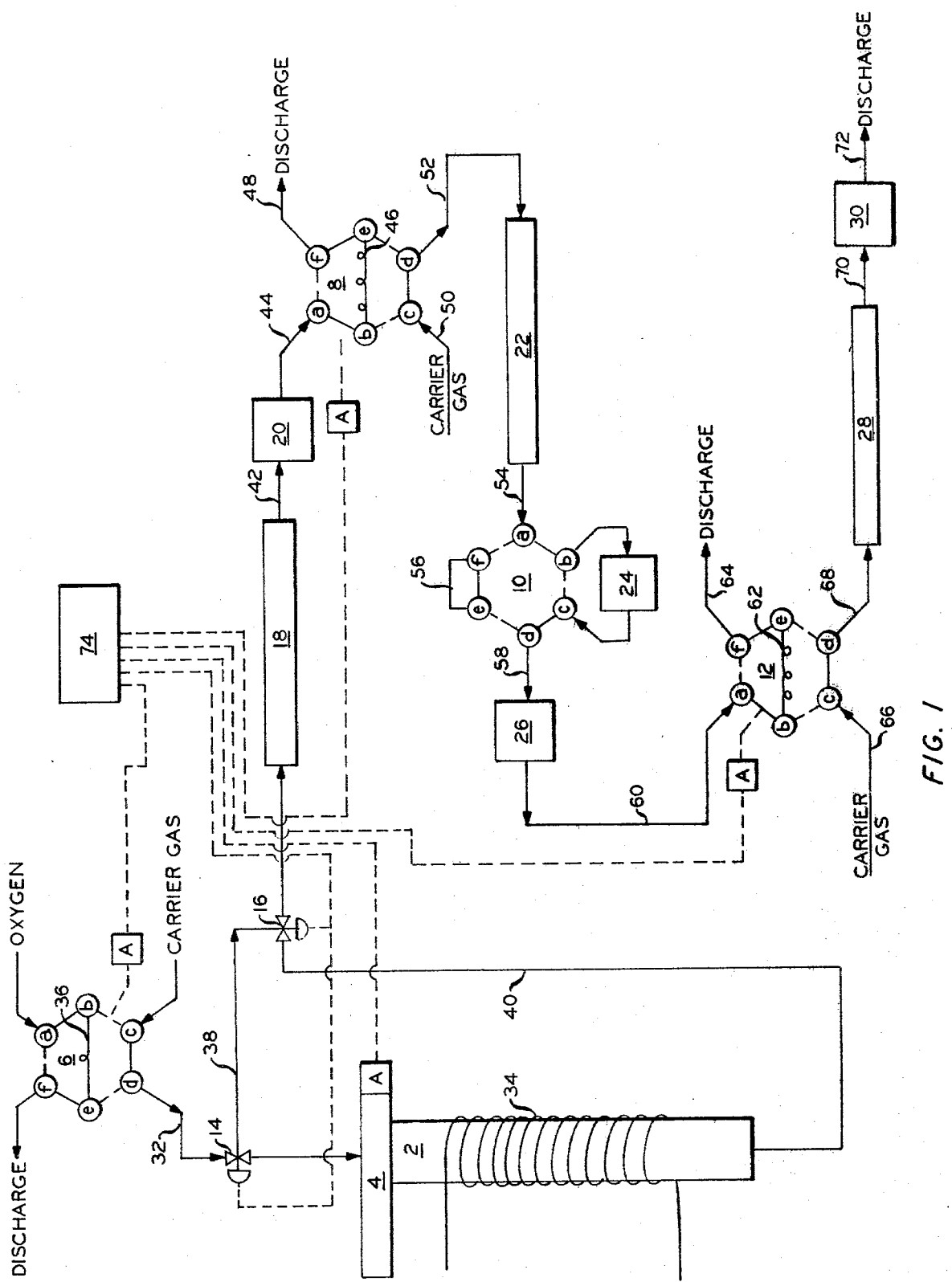
FIG. 1 is a schematic representation of one embodiment of the invention.

Referring now to FIG. 1, therein is illustrated a combustion chamber 2, sample introduction means 4, multiport, multichannel valve means 6, 8, 10 and 12, by-pass valve means 14 and 16, first chromatographic column 18, first detector 20, second chromatographic column 22, peak depressor means 24, second detector 26, third chromatographic column 28 and third detector 30.

An inert carrier gas, such as helium or argon, from a source not shown, is introduced into the combustion chamber 2 through the sample introduction means 4, conduit means 32 and valve means 6. As previously described valve means 6 is a multi-port, multi-conduit valve means. A suitable multi-port valve means is described in U.S. Pat. No. 3,111,849. It is understood by those skilled in the art that the positioning of valve means 6, 8, 10 and 12 can be controlled by conventional timing mechanisms known and generally used in the art of chromatographic analysis.

The multi-port valve means are shown diagrammatically as six port valves with the small circles representing the ports and the straight lines between adjacent ports representing the passages in the core. The solid straight lines between adjacent ports represent the passages in the first position of the valve. The dashed straight lines between adjacent ports represent the passages in the second position of the valve. The ports are designated a-f and are hereinafter referred to by valve number and port letter, such as, for example, port a of valve means 6 is referred to as port 6-a.

In the analysis of a sample for C, H and N, the sample to be analyzed is introduced by sample introduction means 4 into the combustion chamber 2. The sample introduction means can be a conventional indexing sample holder provided with suitable means for sealing the passage between the sample holder and the combustion chamber and between the conduit means 32 and the sample holder.

The combustion chamber 2 is heated by a conventional coil 34. Oxygen, from a source not shown, is supplied via port 6-a at a suitable pressure to conduit means 36. This conduit means 36 has a fixed volume and connects ports 6-b and 6-e. Excess oxygen is discharged through port 6-f, which can be provided with a suitable orifice to maintain the flow of oxygen therethrough constant at a given pressure.

Following introduction of the sample into the combustion chamber 2, the position of valve means 6 is changed. The carrier gas sweeps the oxygen in the conduit means 36 into the combustion chamber 2.

The by-pass valve means 14 and 16 are adapted to be simultaneously turned either to direct the carrier gas to the combustion chamber 2 or to a by-pass conduit means 38. For normal operation, the first setting is used and the carrier gas passes through the combustion chamber 2 and conduit means 40 to the first chromatographic column 18. During the combustion period, to insure complete combustion of the combustible materials in the sample, the carrier gas is passed through the by-pass means 38 to the first column 18.

Following introduction of the fixed volume of oxygen into the combustion chamber, the valve means 14 and 16 are turned to direct the carrier gas to the by-pass conduit 38, thus isolating the combustion chamber 2. After a suitable period of time sufficient to insure essentially complete combustion of the sample, the valve means 14 and 16 are turned to direct the carrier gas into the combustion carrier 2. If desired, the by-pass conduit 38 and the valve means 16 can be omitted. Valve means 14 would then function as a stop valve.

The reaction products in the combustion chamber are swept by the carrier gas through conduit means 40 into the first chromatographic column 18. The major reaction products are, generally, carbon dioxide, water and nitrogen. Other reaction products which may also be present include the hydrogen halides, hydrogen cyanide, sulfur oxides, halogens, hydrogen sulfide, ammonia, carbon monoxide, methane and nitrogen oxides. Oxygen can also be present in the reaction product mixture, either due to an excess of oxygen in relation to the sample or to liberation of oxygen by the sample.

The first chromatographic column 18 is utilized to separate the water vapor and, if present, the hydrogen halides, hyrogen cyanide and sulfur oxides, from the remaining components of the reaction product mixture. The water vapor, hydrogen halides, hydrogen cyanide, hydrogen sulfide and sulfur oxides are hereinafter referred to collectively, as the "water group" of gases. The column 18 can be of any suitable material and packing. Satisfactory results have been achieved using a column packed with porous siliceous particles, such as Porapak Q or Porapak S, both available from Waters Associates, Milford, Mass.

The effluent from the first column 18 is passed via conduit means 42 to first detector means 20. The detector means 20, and similarly detector means 26 and 30, is a conventional means for detecting a property of the fluid mixture directed thereto, which property is representative of the composition of the fluid mixture. Detector means 20 can be a temperature sensitive element disposed in the path of the fluid flow. A reference element, not shown, can be disposed in the carrier gas flow. Such a detector provides signals representative of the difference in thermal conductivity between the column effluent and the carrier gas. The temperature difference between the resistance elements can be measured by an electrical bridge circuit, such as a wheatstone bridge. However, detector means 20 can be any other type of apparatus known in the art for measuring a property of a gaseous stream representative of the composition thereof.

The effluent from the detector means 20 is passed via conduit means 44 to port a of valve means 8, thence to delay means 46, connecting ports 8-b and 8-e. The delay means 46 can be a piece of tubing having an inside diameter D and a length L which can be determined according to the formula:

$$L = (4VX/\pi D^2)$$

where V is the rate of carrier gas flow in milliliters per minute, D is the inside diameter of the tubing in centimeters, and L is the length of the tube in centimeters required to achieve the desired delay X measured in minutes.

In the first position of the valve means 8 the outlet of the delay means 46 is connected internally to discharge port 8-f. Conduit means 48 connects port 8-f with a system discharge, now shown.

Carrier gas from a second source, not shown, is passed via conduit means 50 to port 8-c, thence through the valve means and via conduit means 52 to the second chromatographic column 22.

After the first components of the effluent from the first detector means 20 have passed into the delay means 46 and before the leading component thereof reaches the outlet end of the delay means 46, the valve means 8 is charged to its second position. The carrier gas, from the second source, is now directed to the delay means 46 and sweeps at least a portion of the contents of the delay means 46 into conduit means 52, thence to the second chromatographic column 22. While the valve means 8 is in the second position, the water or other components separated on the first column 18 are directed to the discharge port 8-*f* and pass via conduit means 48 to the system discharge. After a suitable period of time, sufficient to insure that all of the heretofore unanalyzed components have been passed out of the delay means 46 to the second column 22, the valve means 8 is charged to its first position. Any components separated on the first column 18 which may have remained in the delay means 46 are directed to the discharge port 8-*f*.

The second chromatographic column 22 is utilized to separate the carbon dioxide and, if present, the halogens, nitrous oxide, ammonia, and hydrogen sulfide, from the remaining heretofore unanalyzed components of the reaction product mixture. The carbon dioxide, halogens, ammonia and hydrogen sulfide are hereinafter referred to, collectively, as the "carbon dioxide group" of gases. The column 22 can be of any suitable materials and packing. Satisfactory results have been achieved using a column packed with porous siliceous particles, such as Porapak T, available from Waters Associates, Milford, Mass.

In general, the volume of carbon dioxide is quite high as compared to the other components of a reaction product mixture. The carbon dioxide peak height often can exceed the capacity of the detector means and/or the instrument recording the value detected. Provision is made, therefore, for depressing the carbon dioxide peak height, when necessary, by diluting the separated components with the carrier gas. The effluent from the second column 22 is passed via conduit means 54 to valve means 10. Valve means 10 has a peak depressing means 24 connected across ports 10-*b* and 10-*c*, and a by-pass conduit 56 connected across ports 10-*e* and 10-*f*.

When the volume of carbon dioxide in the reaction product mixture is high the valve means 10 can be left in the position shown. The effluent from the second column then passes through the peak depressing means 24. When the volume of carbon dioxide is low or wheen it is desired to obtain greater resolution of other components separated on column 22, the valve means 10 can be changed to its second position (shown by the dashed lines) and the effluent passes through the by-pass conduit 56. The peak depressing means 24 is a serially connected chamber having a sufficient volume so related to the flow rate of the carrier gas to allow mixing of the carbon dioxide and the carrier gas, thus diluting the carbon dioxide, thereby lowering the peak height.

The effluent from the valve means 10 is passed via conduit means 58 to second detector means 26, thence via conduit means 60 to port 12-*a* of valve means 12. This effluent is directed to delay means 62, connecting ports 12-*b* and 12-*e*. The delay means 62 is similar to configuration and function to delay means 46.

In the first position of the valve means 12, the outlet of the delay means 62 is connected internally to discharge port 12-*f*. Conduit means 64 connects port 12-*f* with a system discharge, not shown.

Carrier gas from a third source, not shown, is passed via conduit means 66 to port 12-*c*, through the valve means 12, thence via conduit means 68 to the third chromatographic column 28.

After the first components of the effluent from the second detector means 26 have passed into the delay means 62 and before the leading component thereof reaches the outlet end of the delay means 62, the valve means 12 is changed to its second position. The carrier gas, from the thid source, is now directed to the delay means 62 and sweeps at least a portion of the contents of the delay means 62 into conduit means 68, thence to the third column 28. While the valve means 12 is in the second position, the carbon dioxide and, if present, other components separated on the second column 22 are directed to the discharge port 12-*f* and pass via conduit means 64 to the system discharge. After a suitable period of time, sufficient to insure that all of the heretofore unanalyzed components have been passed out of the delay means 62 to the third column 28, the valve means 12 is changed to its first position. Any components separated on the second column 22 which may have been in the delay means 62 are directed to the discharge port 12-*f*.

The third chromatograhic column 28 is utilized to separate the nitrogen, and if present, oxygen, methane, carbon monoxide and nitrogen oxides. These gases are hereinafter referred to, collectively, as the "nitrogen group" of gases. The column 28 can be of any suitable material and packing. Satisfactory results have been achieved using a column packed with molecular sieves.

The effluent from the third column is passed via conduit means 70 to third detector means 30, thence via conduit means 72 to the system discharge.

Figure 2:
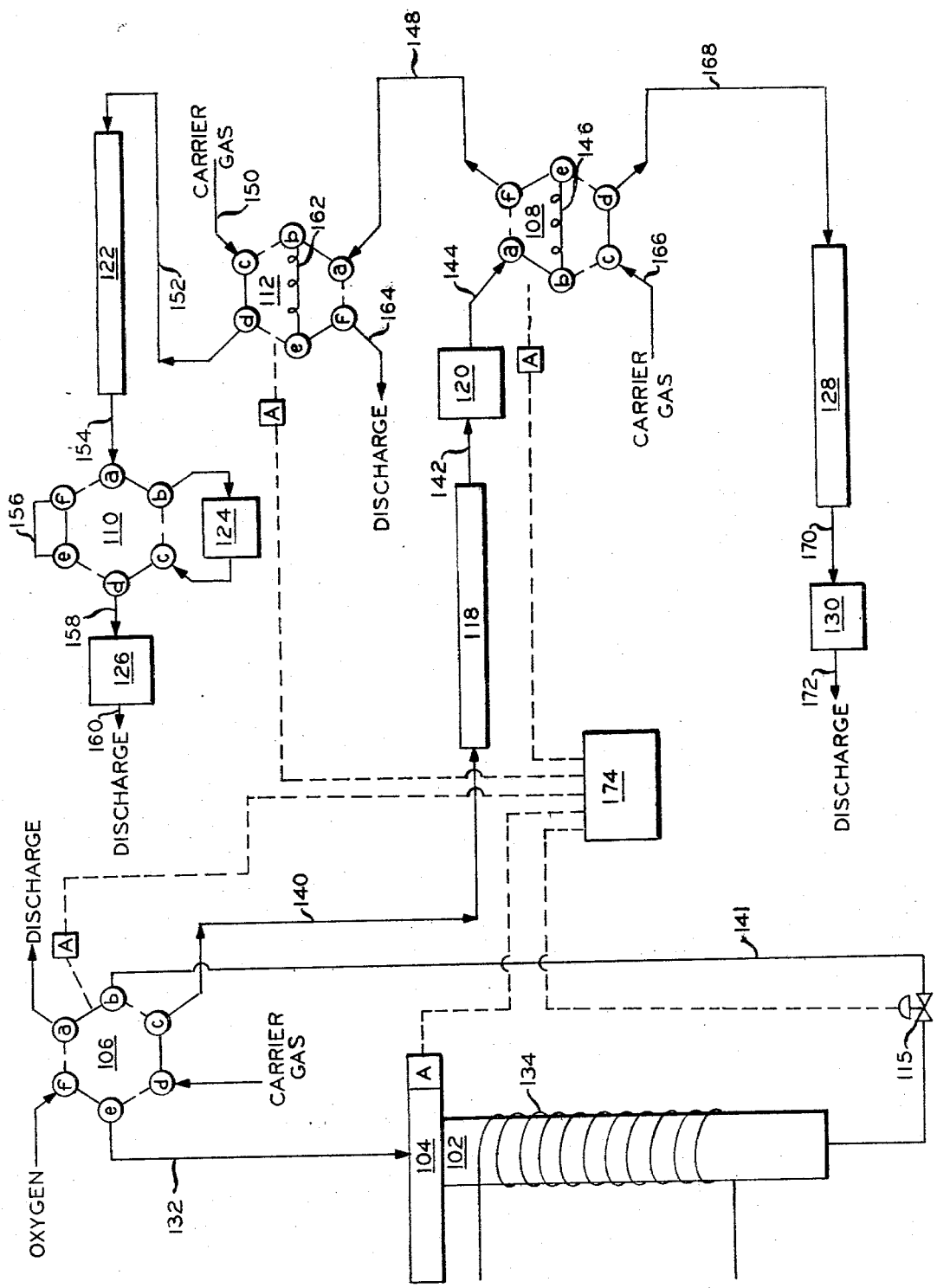
FIG. 2 is a schematic representation of another embodiment of the invention.

FIG. 2 represents an alternative arrangement which can be used when the nitrogen group gases described previously, is adequately separated from the carbon dioxide group gases, described previously, on the first chromatographic column 118. FIG. 2 also shows an alternative arrangement for combusting the sample and introducing the combustion gases into the first chromatographic column 118. As shown in FIG. 2, the first carrier gas is introduced to valve means 106, which can be a multi-port, multichannel valve means as previously described. In the first position of valve means 106, shown by the solid lines, the carrier gas is directed through conduit means 140 to the first chromatographic column 118.

Oxygen, from a source not shown, is supplied via port 106-*f* to conduit means 132, thence to the combustion chamber 102. The effluent from the combustion chamber is passed via conduit means 141 to port 106-*b* of valve means 106. Port 106-*b* is connected internally to discharge port 106-*a*. Conduit means 141 has a flow stop valve means 115 to prevent flow therethrough.

A sample to be analyzed is introduced by sample introduction means 104 into the combustion chamber 102. Chamber 102 is heated by a conventional coil 134. Following introduction of the sample into the combustion chamber 102, the position of valve means 115 is changed to stop the flow of gases through the combustion chamber 102. Following a suitable combustion period, the position of valve means 106 is changed and the valve means 115 is opened. The carrier gas is directed through the conduit means 132 into the combustion chamber 102. The reaction products in the combustion chamber are swept by the carrier gas through conduit means 141, valve means 106 and conduit means 140 into the first chromatographic column 118.

The effluent from the first chromatographic column 118 is passed via conduit means 142 to the first detector means 120. The effluent from the first detector means 120 is passed via conduit means 144 to port a of valve means 108, thence to delay means 146, connecting ports 108-*b* and 108-*e*.

In the first position of the valve means 108 the outlet of the delay means 146 is connected, internally, to port 108-*f*. Conduit means 148 connects port 108-*f* with valve means 112.

Carrier gas, from a source, not shown, is passed via conduit means 166 to port 108-e, thence through the valve means and via conduit means 168 to column 128. Column 128 is utilized to separate the nitrogen group gases.

After the nitrogen group gases from the first detector means 120 have passed into the delay means 146 and before the leading component of the carbon dioxide group gases reaches the inlet of the delay means 146, the valve means 108 is changed to its second position. The carrier gas, from the second source, is now directed to the delay means 146 and sweeps the contents of the delay means 146 into the conduit means 168, thence to column 128. The valve means 108 is maintained in the second position until all of the carbon dioxide group gases and the water group gases have passed completely therethrough.

The column 128 is utilized to separate the nitrogen group gases, as previously described. The effluent from column 128 is passed via conduit means 170 to detector means 130, thence via conduit means 172 to the system discharge.

Carrier gas, from a source not shown, is passed via conduit means 150 to port 112-c of valve means 112, thence through the valve means and via conduit means 152 to column 122.

As previously described, the carbon dioxide group gases and the water group gases eluting from detector means 120 are passed directly through valve means 108. Conduit means 148, connecting valve means 108 and 112 conducts these gases to port 112-a of valve means 112. The gases are passed to delay means 162.

In the first position of valve means 112 the outlet of delay means 162 is connected internally to discharge port 112-f. Conduit means 164 connects port 112-f with a system discharge, not shown.

After the components of the carbon dioxide group gases have passed into the delay means 162 and before the leading component thereof reaches the outlet end of the delay means 162, the valve means 112 is changed to its second position. The carrier gas in conduit means 150 is now directed to the delay means 162 and sweeps the carbon dioxide group gases into conduit means 152, thence to column 122. After a suitable period of time, sufficient to insure that all of the carbon dioxide group gases have been passed out of the delay means 162 to column 122, the valve means 112 is changed to its first position.

The column 122 is utilized to separate the carbon dioxide group gases, as previously described. The effluent from the column 122 is passed via conduit means 154 to valve means 110, thence through peak depressor means 124, or through by-pass conduit 156, as previously described. The gases are then passed via conduit means 158 to detector means 126. The effluent from detector means 126 is passed via conduit means 160 to the system discharge.

The positions of the various valve means can be controlled by timing means 74 and 174, shown in FIGS. 1 and 2, respectively. Such timing means are known in the art. The timing means controls actuating means, designated A, at each valve and at the sample introduction means.

Referring again to FIG. 1, in the analysis of a sample for elemental sulfur and/or oxygen, outside oxygen is not used, and the chamber 2 contains carbon and, optionally, platinum gauze. The sample to be analyzed is introduced by sample introduction means 4 into chamber 2. After a suitable period of time sufficient to insure substantially complete pyrolysis of the sample, the valve means 14 and 16 are turned to direct the carrier gas into chamber 2.

The pyrolysis products in chamber 2 are swept by the first carrier gas through the carbon and the optional platinum gauze, either sequentially or simultaneously, then through conduit means 40 into the first chromatographic column 18.

The carbon employed in chamber 2 can be any form of carbon which will react with carbon dioxide, water and the sulfur oxides to form carbon monoxide, as discussed previously, such as carbon black, graphite and the like. It has been found that carbon black is superior for the conversion of oxygen to carbon monoxide, but it retains sulfur too long. On the other hand, graphite releases the sulfur quickly, but leaves part of the oxygen as water. The water peak can, of course, be measured, so this does not negate the use of graphite.

In the analysis for sulfur the platinum gauze is not used.

In the analysis for oxygen, the first chromatographic column 18 is used to separate water vapor and, if present, the hydrogen halides, hydrogen cyanide and sulfur oxides, from the remaining components of the reaction product mixture. The column 18 can be any suitable material and packing. Satisfactory results have been achieved using a column packed with porous siliceous particles, such as the Porapak material referred to previously.

Because of the major portion of carbon dioxide which may have originally been present in the pyrolysis reaction mixture is converted by reacting same with carbon, the second chromatographic column 22 can be any suitable material which will satisfactorily separate carbon monoxide and any residual carbon dioxide. Satisfactory results have been achieved using a column packed with a mixture of charcoal and molecular sieves.

When analyzing solely for oxygen, the third chromatographic column 28 its associated valve means 62 and detector means 30 can be omitted, if desired.

In the analysis for sulfur, or for sulfur and oxygen, column 18 is also used to separate water vapor, as above. The packing materials disclosed above can be used. The second column 22 is used to separate residual carbon dioxide and hydrogen sulfide. Column 22 can be any suitable packing material, such as the Porapak material referred to previously. The third column 28 is used to separate the carbon monoxide. Column 28 can be a charcoal/molecular sieve column, as above.

Optionally, the analysis for sulfur, or for sulfur and oxygen, can be made using two chromatographic columns, i.e., a porous siliceous column for separating hydrogen sulfide, followed by a charcoal/molecular sieve column for separating carbon monoxide.

The method of this invention involves two distinct modes: first, a sample to be analyzed is combusted, in the presence of added oxygen, and second, the sample to be analyzed is pyrolyzed, in the absence of added oxygen.

In the combustion mode, the sample and oxygen are introduced into the combustion chamber and, after combustion is complete, the reaction products are swept into the first chromatographic column. If desired, the combustion reaction products can be passed over hot nickel oxide to insure complete combustion. If further desired, the reaction product mixture can be passed over hot copper to absorb excess oxygen.

In the pyrolysis mode, the sample alone is introduced into the combustion chamber, and after pyrolysis is complete, the reaction products are swept into the first chromatographic column.

The method and apparatus of this invention have been found to be particularly useful for determining the carbonate carbon, total carbon and organic carbon contents of geological samples. The total carbon is determined by introducing a weighed sample into the combustion chamber, admitting oxygen to the chamber, and passing the combustion products through the chromatographic apparatus. To determine the carbonate carbon, the sample must first be decarbonated, then analyzed as before, to obtain the value for organic carbon. The carbonate carbon is determined by subtracting the organic carbon from the total carbon.

The sample to be analyzed can be decarbonated by a wet acid treatment with hydrochloric acid or by treatment with hydrogen chloride vapor, the vapor phase treatment being preferred. The vapor phase treatment offers several definite advantages over the wet acid treatment generally used, because (1) it is difficult to wet small samples and (2) there is a strong possibility that carbon dioxide is trapped within packets within the wetted mass. Vapor phase decarbonation allows unattended treatment of a large number of samples and, the samples need not be heated, as is required by the wet acid method.

To carry out the vapor phase treatment, the samples are first exposed to water vapor. The samples are then allowed to stand over 32–34 percent hydrochloric acid or are surrounded with hydrogen chloride vapor under pressure, e.g., 100 psi or greater.

Three additional aspects of the invention involve (1) the use of gas permeation tubes to condition the apparatus with respect to certain atoms and/or molecules, (2) a combustion tube which provides more complete combustion of samples as compared to prior art combustion tubes, and (3) the use of a delay volume and a reduction chamber for improved analysis of combusted samples.

In some instances it may be desirable to expose the chromatographic apparatus to one or more conditioning gases prior to analyzing a sample in accordance with another aspect of the invention. Such an instance exists, for example, if the sample, after combustion or pyrolization, produces one or more atoms or molecules which tend to be adsorbed by the various component parts of the chromatographic apparatus which in turn results in low, inaccurate and erroneous results. The adsorption problem can be overcome in accordance with the invention by exposing the chromatographic apparatus to a source of certain atoms or molecules prior to analyzing the sample which is accomplished by using one or more conditioning gases containing all the atoms or molecules present in the sample which would otherwise be adsorbed by the various components of the chromatographic apparatus. Generally the one or more conditioning gases are added to the carrier gas and to the oxygen gas used for combustion of a sample or the hydrogen gas used for pyrolysis of a sample by using gas permeation tubes. Gas permeation tubes release a specific gas at a known rate. Gas permeation tubes per se are well known in the art and available from various suppliers, such as for example Metronics Associates, Santa Clara, Ca. A gas permeation tube can be obtained which releases a gas selected from a variety of gases such as sulfur dioxide, hydrogen sulfide, and carbon tetrachloride for example.

Figure 3:
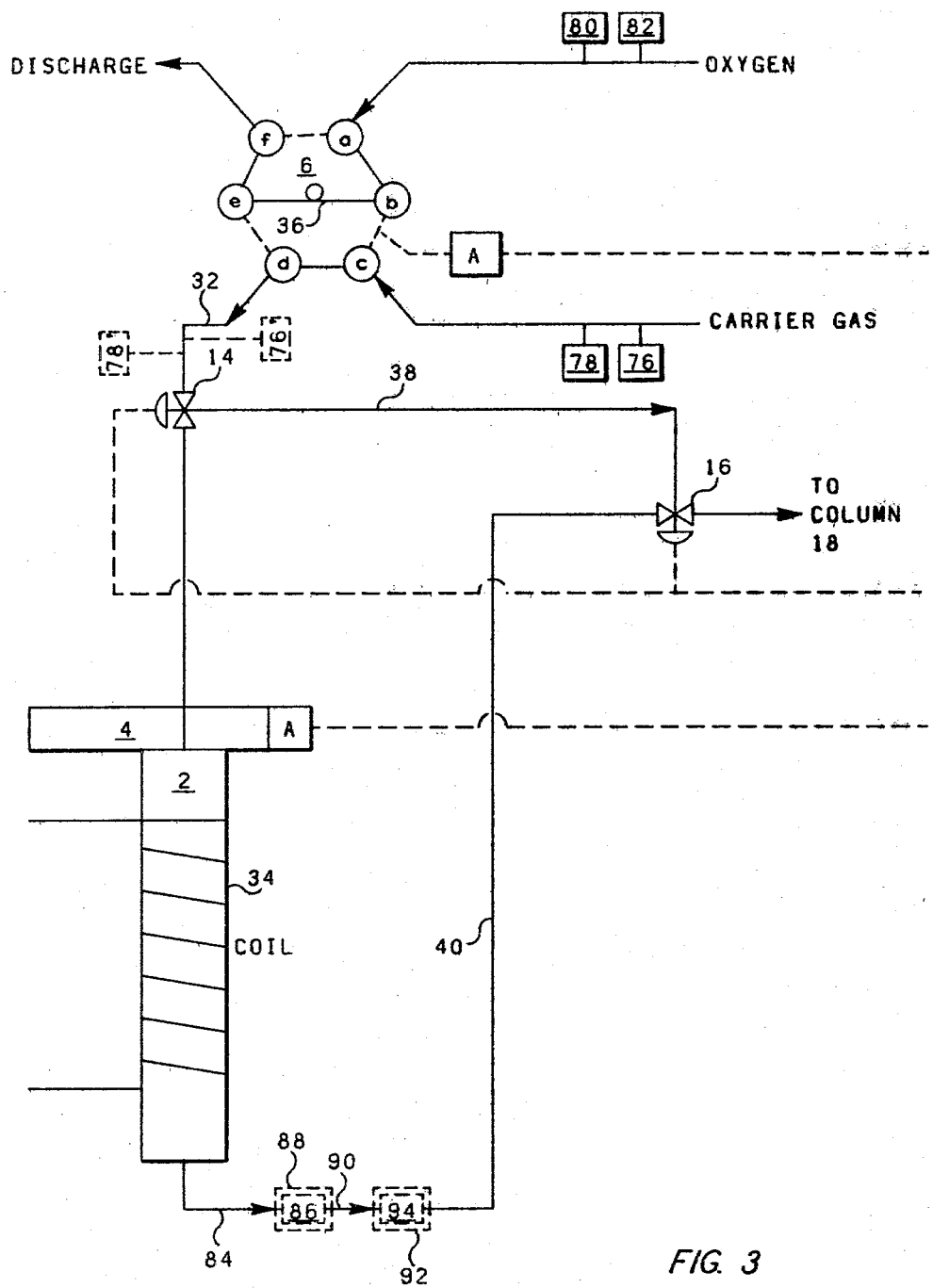
FIGS. 3 and 5 illustrate two other embodiments of this invention which are modifications of the embodiment of FIG. 1 in which only that part differing from the embodiment of FIG. 1 are shown.

Referring to FIG. 3, a portion of the apparatus of FIG. 1 is modified to show the use of a gas permeation tube 76 which adds a first conditioning gas at a specific rate to the carrier gas and another gas permeation tube 80 which adds the first conditioning gas at the same specific rate to the oxygen gas. An alternative arrangement also is shown wherein only one gas permeation tube is used for each conditioning gas which is positioned in communication with conduit means 32, such as gas permeation tube 76'. In a specific illustration, if the combustion of a sample could result in the production of sulfur dioxide gas, gas permeation tubes 76 and 80 are sulfur dioxide gas permeation tubes. Gas conditioning means 78 and 82 can be additional gas permeation tubes such as carbon tetrachloride gas permeation tubes or any other chlorine-emitting permeation tube if for example the particular sample was to be analyzed for chlorine. As another alternative gas conditioning means 78 and 82 could be water vapor emitting devices for introducing water vapor into the system in the carrier gas and oxygen. Good results have been obtained when testing a sample for sulfur dioxide by using sulfur dioxide gas permeation tubes in combination with water vapor emitting devices. It is noted that a single water vapor emitting device and/or a single carbon tetrachloride gas permeation tube could be positioned in conduit means 32 such as means 78' instead of using two such devices, one positioned in the oxygen such as means 82 and one positioned in the carrier gas supply means such as means 78.

Figure 5:
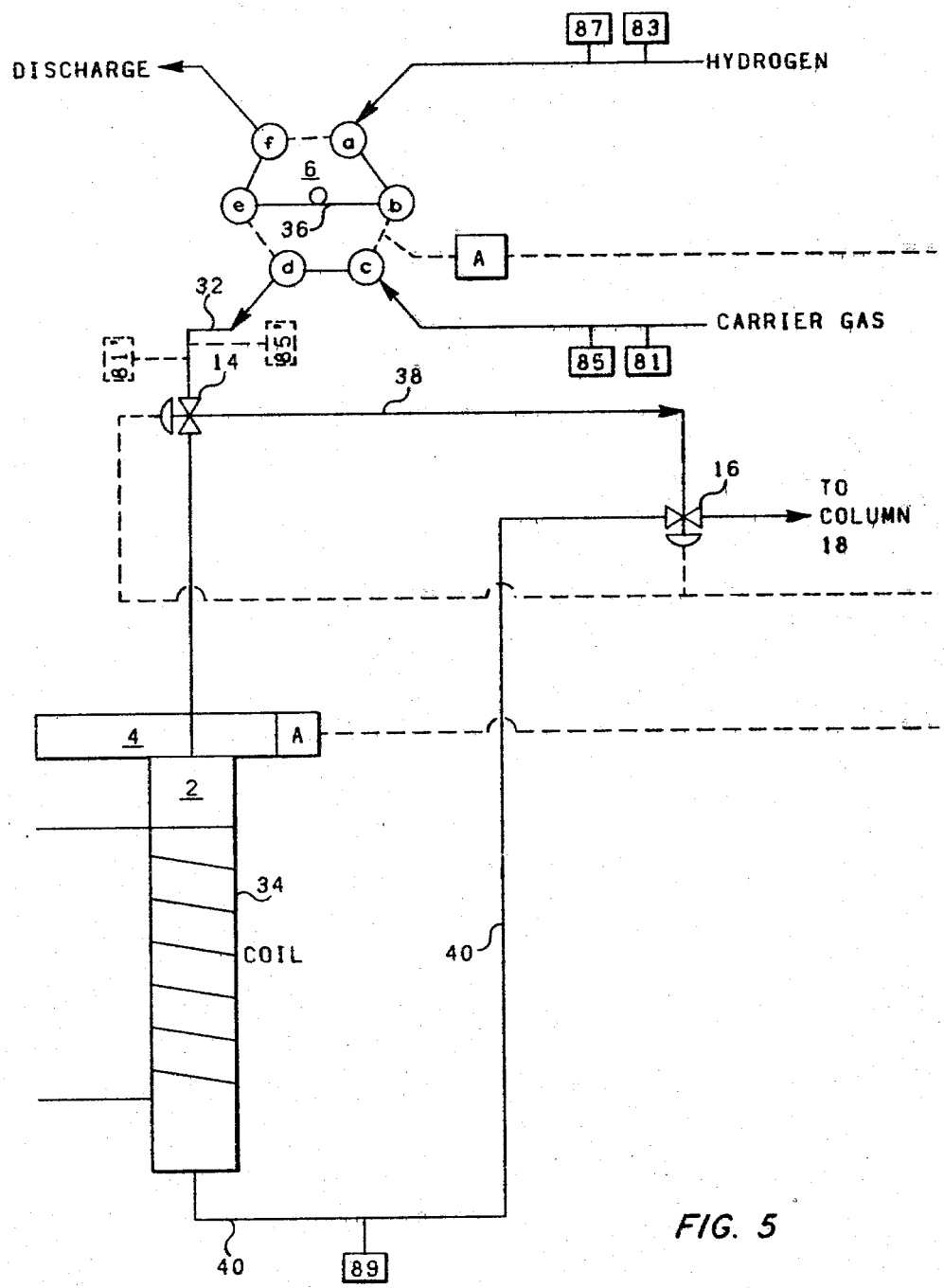

FIG. 5 is similar to FIG. 3 in that FIG. 5 is also a modification of a portion of FIG. 1; however, the embodiment of FIG. 5 shows a device which is useful when the sample to be analyzed is to be subjected to pyrolysis rather than combustion. In such case, a source of hydrogen rather than oxygen is used and if for example the sample is to be analyzed for sulfur, hydrogen sulfide gas permeation tubes are used rather than sulfur dioxide gas permeation tubes described in connection with FIG. 3. As in the case of FIG. 3, an alternative arrangement is the use of one gas conditioning device 85' in conduit means 32 rather than using one device 87 for introducing the conditioning gas in the hydrogen gas and another device 85 for introducing the conditioning gas in the carrier gas. FIG. 5 shows the use of two separate gas conditioning devices 83, 87 for the hydrogen gas and two separate gas conditioning devices 81, 85 for the carrier gas or alternatively gas conditioning devices 81', 85' can be used. While FIGS. 3 and 5 show the use of two gas conditioning devices, the invention includes the use of one or more such devices and two such devices are shown only for purposes of illustration.

Figure 4:
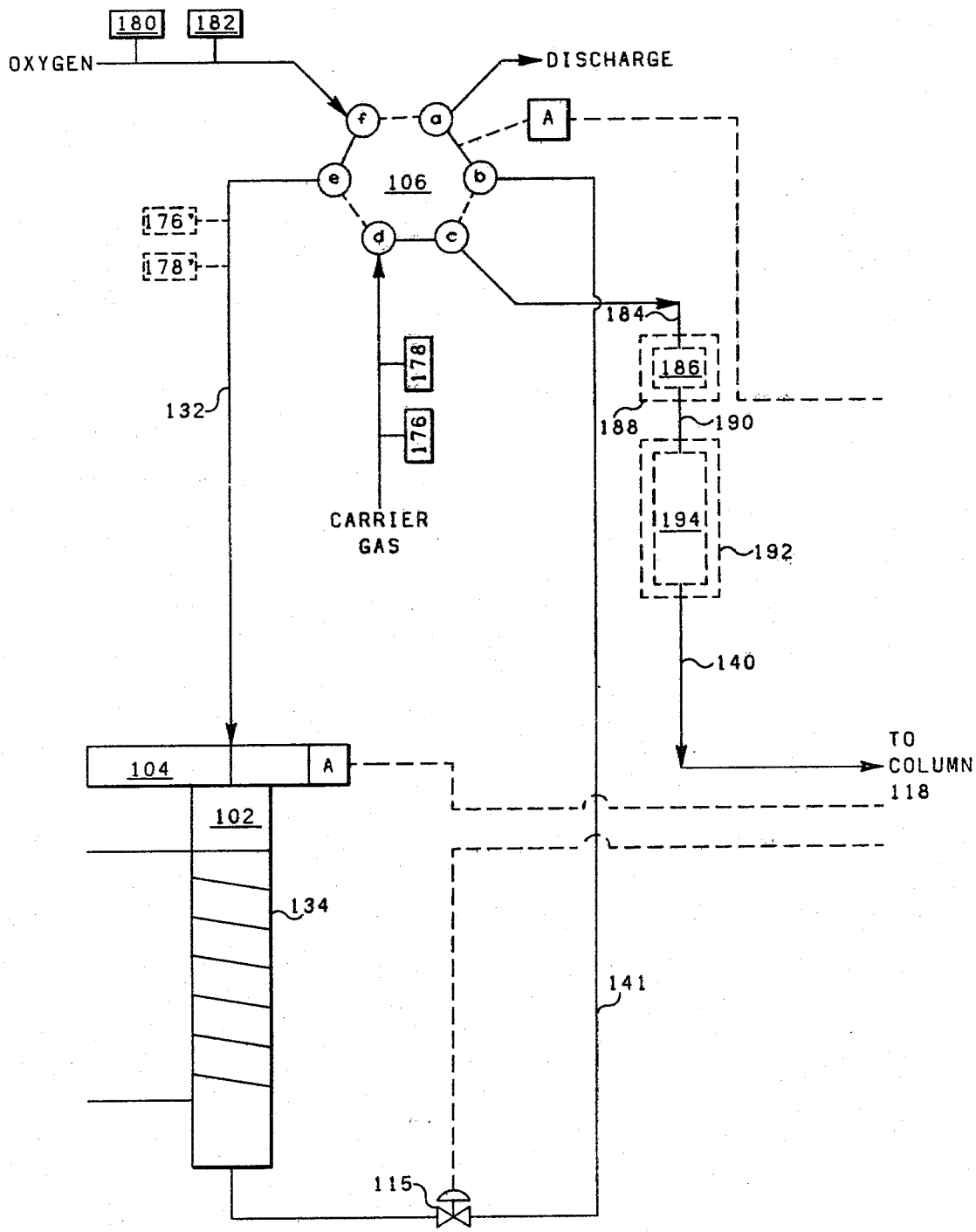
FIGS. 4 and 6 illustrate two other embodiments of this invention which are modifications of the embodiment of FIG. 2 in which only that part differing from the embodiment of FIG. 2 are shown.

FIG. 4 shows the modification of a portion of the apparatus of FIG. 2 in the same way that FIG. 3 is a modification of a portion of FIG. 1. In particular 178 and 182 are gas conditioning means such as sulfur dioxide gas permeation tubes. 176 and 180 correspond to a different source of conditioning gas such as carbon tetrachloride gas permeation tubes or water vapor emitting devices. 178' and 176' correspond to an alternative arrangement similar to that previously discussed in connection with FIGS. 3 and 5. In the alternative arrangement 178' represents the position of the gas conditioning device in conduit means 132 which replaces devices 178 and 182. 176' likewise replaces 176 and 180.

Figure 6:
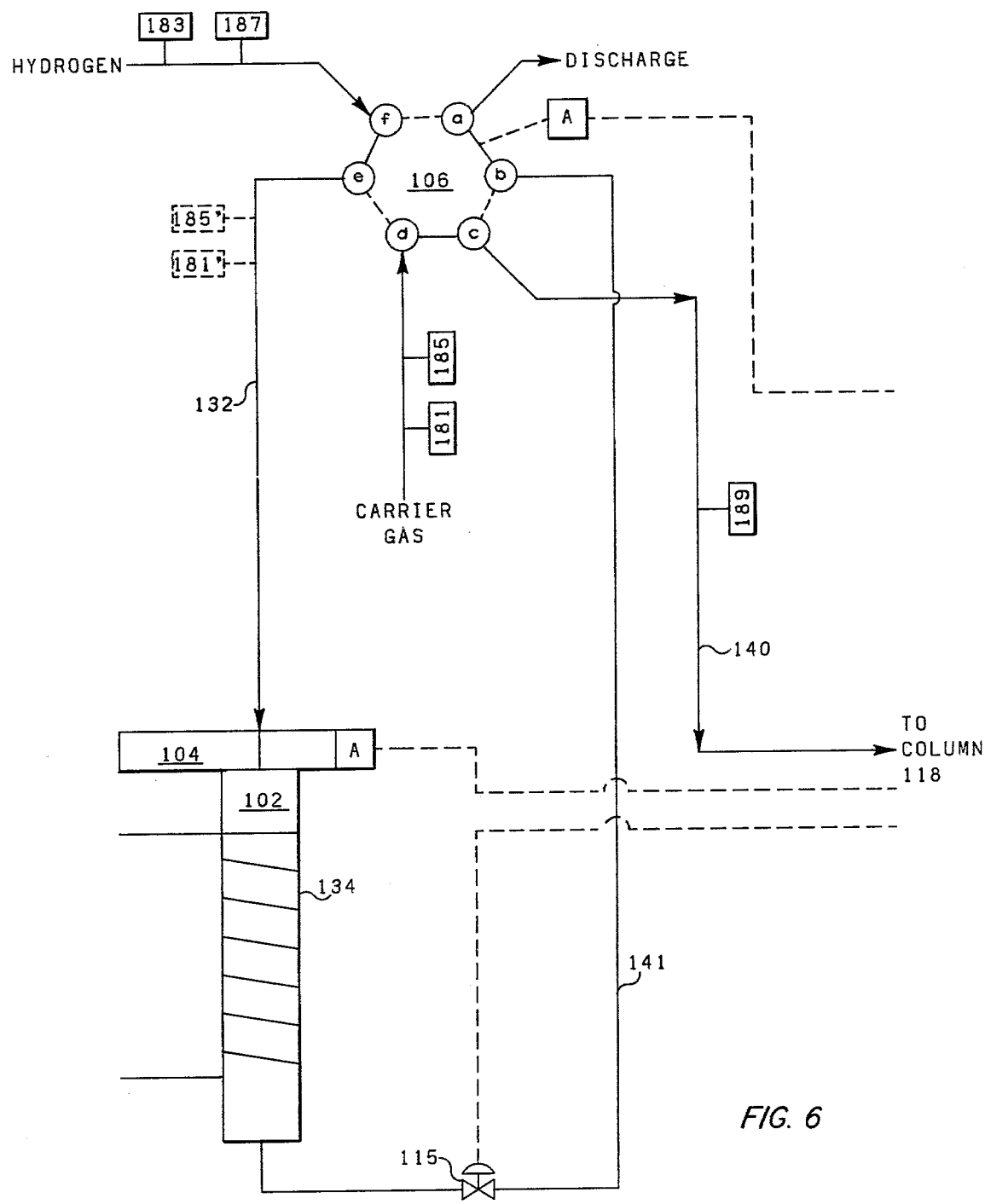

FIG. 6 corresponds to FIG. 4 in the same way that FIG. 5 corresponds to FIG. 3. Specifically, FIG. 6 shows a device useful for the pyrolysis of a sample in which a source of hydrogen is supplied to port f of valve 106 rather than a source of oxygen is shown in FIG. 4. Also gas conditioning devices such as 181 and 183 or the alternative 181', and 185 and 187 or the alternative 185' are shown. From the previous discussion it is apparent that 181, 183 and 181' can be hydrogen sulfide gas permeation tubes and 185, 187 and 185' can be carbon tetrachloride gas permeation tubes.

When pyrolysis of a sample is desired using the devices of FIGS. 5 and 6 it is preferable to use a water vapor emitting device 89 and 189 respectively for introducing water vapor into the system via conduit means 40 and 140 respectively.

If it is desired to add water vapor to the system shown in FIGS. 3 through 6, any vessel or device which introduces water vapor into the desired gas stream can be employed in the apparatus. Satisfactory results have been achieved using a T-shaped vessel to introduce water vapor into the desired gas stream wherein water is contained in the vertical portion of the "T" and wherein the gas to which the water vapor is added flows through the horizontal portion of the "T" to contact the water vapor.

In the quantitative measurement of samples by gas chromatography, there is a need for a combustion chamber that not only completely combusts the sample but also is operable in a continuous gas chromatographic system. As known by those skilled in the art prior art combustion chambers frequently do not completely combust the sample. Moreover, these combustion chambers are not useful in a continuous system without either cleaning the residue contained in the combustion chamber or installing a new combustion chamber. Obviously, in the combustion of a number of individual samples, combustion residues accumulate in the chamber. A buildup of residues in the chamber can hinder or block the flow of gases from the chamber. And, in the analysis of samples, it is necessary that a constant flow rate of gases be maintained since an unwanted fluctuation in gas flow rate can adversely affect response factors in a gas chromatographic system.

As a consequence, the development of a combustion chamber that will at least approach complete combustion of a sample and yet be conveniently utilized in a continuous gas chromatographic system is highly desired.

Figure 7:
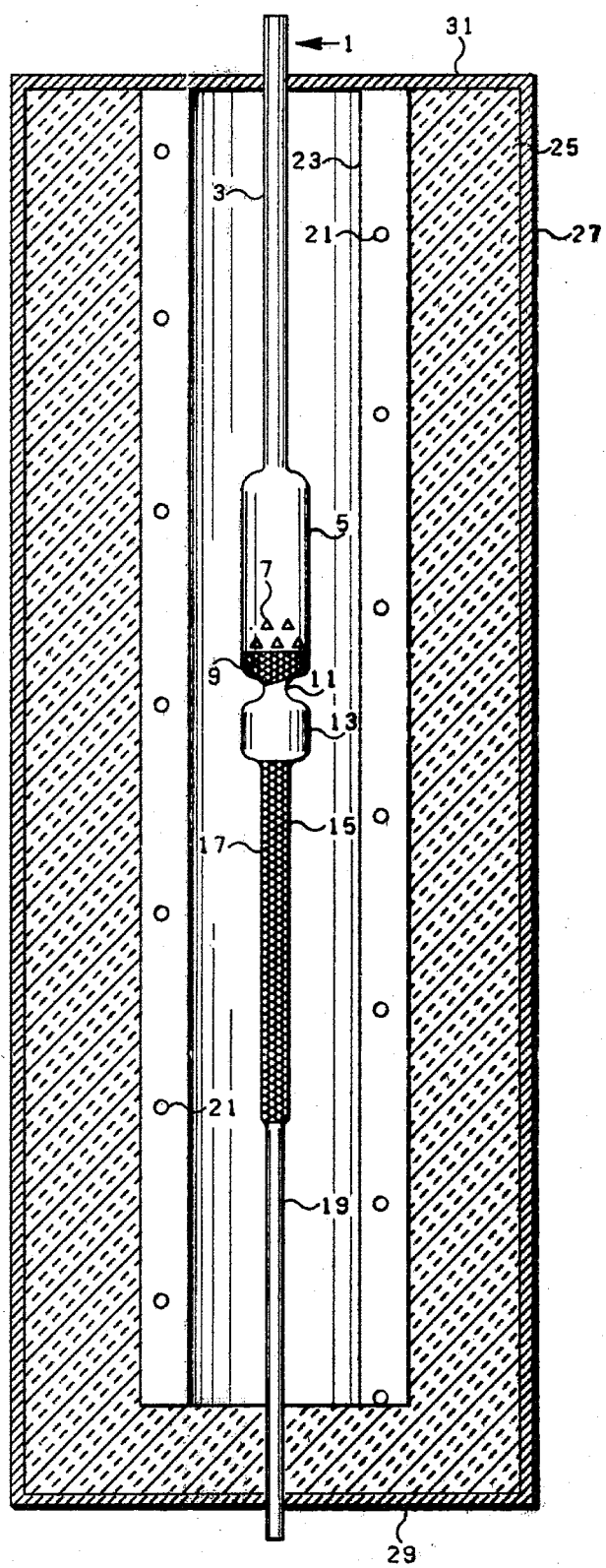
FIG. 7 is an elevational view of a preferred embodiment of the combustion chamber of the invention installed in a furnace in which the furnace is shown in cross section.

Referring to FIG. 7, a preferred embodiment of such a combustion chamber is shown. A combustion tube indicated generally by reference numeral 1 is an elongated conduit that is suitable for passing a substance therethrough. An elongated inlet means 3 is provided to pass a sample into the first chamber 5. The length of inlet means 3 must be of sufficient length to preclude the condensation of combustion gas on the walls thereof when combustion tube 1 is used for the oxidative decomposition of a sample in a gas chromatographic analyzer. The volume of first chamber 5 can vary according to the number of samples desired to be placed therein. However, it is presently preferred for regular analytical operations that said first chamber 5 have a volume in the range of about 20 to about 50 cubic centimeters (cc). A constricted passageway 11 separates the first chamber 5 from the second chamber 13 and functions primarily to separate first chamber 5 from said second chamber 13. Thus, the length and diameter of said passageway is not deemed to be critical. Positioned near the second chamber 13 is a layer of inert packing 9.

When combustion tube 1 is employed in the oxidative decomposition of a sample, inert packing 9 should have a melting point of at least 1200° C. Good results were obtained using an inert packing of quartz wool which is preferred. While inert packing 9 primarily functions to support the inert subdivided substance 7 in FIG. 7 inert packing 9 could use to form the common wall of the first chamber 5 and said second chamber 13 so that passageway 11 actually could be eliminated. Variations in the form, size and material of the inert subdivided substance 7 are possible. Specific materials include, such as for example quartz or ceramic particles. Inert substances having a melting point of at least 1200° C. have been found to be particularly satisfactory when the combustion tube 1 is employed in the oxidative decomposition of a sample. While size of the substance is not deemed to be critical, a particle size in the range of about 40 mesh (US Standard Sieve Series) to about ¼ inch diameter is recommended. A presently preferred inert subdivided substance is a quartz chip having a melting point of at least 1200° C. and ⅛ inch diameter. At least one inert subdivided substance 7 is used to prevent the combustion residues from packing. By adding a multitude of inert subdivided substances 7 to the first chamber 5, the combustion residues that accumulate in a continuous system will not pack and a tortuous pathway will be provided by which the combustion gases will be able to pass through to the second chamber 13. The volume of second chamber 13 can vary widely. However, it is presently preferred that second chamber 13 when employed in the oxidative decomposition of a sample have a volume in the range of about 5 to about 10 cubic centimeters. When employed in the oxidative decomposition of a sample, second chamber 13 is primarily an oxygen-containing reservoir. Any gases passing into second chamber 13 that are not completely combusted in the first chamber 5 will be completely combusted in said second chamber 13. Damping chamber 15 is positioned between and in communication with said second chamber 13 and outlet means 19. Damping chamber 15 functions to prevent any large changes in flow rate of the combustion gases during combustion downstream of the combustion tube. Drastic changes in flow rate are to be avoided since the response and accuracy of the instrument are affected. At least a portion of said damping chamber 15 contains an inert packing 17. Said inert packing has a melting point of at least 1200° C. The presently preferred inert packing is quartz wool. While a combustion tube within the scope of the present invention does not require a damping chamber, a damping chamber is recommended for best results. Any conventional heating device such as for example a furnace, can be employed to heat the combustion tube 1. A particularly suitable heating device is shown in FIG. 7. Combustion chamber 1 is positioned inside a ceramic cylinder 23 having electrical resistant heaters 21. Said electrical resistant heaters 21 are longitudinally spaced throughout the walls of said cylinder 23. Positioned between the outer wall 27 and the top 31 and the bottom 29 is thermal insulation 25.

The combustion tubes of the invention as described above are suitable for use in the apparatus and process of FIGS. 1 to 4 previously described.

In accordance with the process of the invention employing the combustion tube 1 of FIG. 7 as combustion tube 2 in FIG. 1 or as combustion tube 102 in FIG. 2 for oxidatively decomposing a sample, oxygen is passed into a first heated combustion zone, combustion chamber 5, and into a second heated combustion zone, combustion chamber 13, to substantially fill each zone with oxygen. A sample to be analyzed by chromatographic analysis after combustion is passed through the elongated inlet means 3 into a first heated combustion zone and the sample is converted to gases which are at least partially oxidatively decomposed in the first combustion zone. The gases of the sample including both oxidatively decomposed gases and ureacted gases are passed to the second combustion zone containing additional oxygen which ensures essentially complete combustion of the sample gases by passing carrier gas into the first heated combustion zone which sweeps the gases from the first heated combustion zone and into the second heated combustion zone. The carrier gas is directed to the combustion tube through ports c and d of valve 6, conduit means 32 valve means 14 and sample introducing means 4 of FIG. 1 or through ports d and e of valve 106, conduit means 132 and sample introduction means 104 of FIG. 2. The oxidatively decomposed sample gases are passed through dampening chamber 15 which prevents any sudden changes in flow rate of the gases down stream of the combustion tube and then the oxidatively decomposed sample gases are passed through outlet means 19 and into the analysis section of the system (not shown) by the purging action of the carrier gas passing through the combustion tube.

In a preferred embodiment which is essentially the combustion chamber shown in FIG. 7, combustion tube 1 is a elongated cylindrical quartz glass conduit. Elongated inlet means 3 is about 63 millimeters (16 inches) in length and 12 millimeters (mm) Outer Diameter (O.D.)×8 mm. Inner Diameter (I.D.). The first chamber 5 is about 11.8 mm. (3 inches) in length and 22 mm. O.D.×18 mm. I.D. The constricted passageway 11 is 0.98 mm. (¼ inch) in diameter and connects said first chamber 5 with said second chamber 13. First chamber 5 contains quartz wool having a melting point of at least 1200° C. The quartz wool is positioned near the second chamber 13 and substantially covers the inlet of constricted passageway 11. The quartz wool supports a number of quartz chips about ⅛ inch diameter and having a melting point of at least 1200° C. The second chamber is about 3.9 mm (1 inch) in length and 18 mm. I.D.×22 mm. O.D. Dampening chamber 15 is positioned between and in communication with said second chamber 13 and outlet means 19. The damping chamber is about 15.7 mm. (4 inches) in length and 12 mm. O.D.×8 mm. I.D. Dampening chamber 15 is essentially filled with quartz wool having a melting point of at least 1200° C. Outlet means 19 is about 23.6 mm. (6 inches) in length and 6 mm. O.D.×5 mm. I.D.

Referring again to FIGS. 3 and 4 the optional use of a delay volume and a reduction chamber will be described. In FIG. 3 the reaction products produced in the combustion chamber 2 are swept by the first carrier gas through conduit means 84 into optional delay volume means 86, through conduit means 90 into optional reduction chamber 94 which contains hot copper and through conduit means 40 into the first chromatography column 18.

The delay volume means 86 is a device for preventing the entrance of excess oxygen into said reduction chamber 94 until the combustion of the sample in said combustion chamber 2 is substantially complete. Without the delay volume means 86, any excess oxygen not utilized in the combustion chamber 2 reaches the reduction chamber before the combustion process is substantially complete and reacts with the hot copper contained in said reduction chamber. As a result of the reaction between the hot copper and the oxygen, a partial vacuum is produced in said reduction chamber which draws incompletely combusted materials out of the combustion chamber. The presence of delay volume means 86 prevents the entrance of excess oxygen into the reduction chamber until the combustion process in the combustion chamber 2 is substantially complete. The partial vacuum then produced by the reaction of the excess oxygen with the hot copper has not been found to have a detrimental effect on the resultant data.

The delay volume means 86 may be no more than a straight piece of tubing but must have a volume at least as great as the volume of oxygen introduced into said combustion chamber 2. Preferably, delay volume means 86 is a helically-shaped quartz tube having a volume of approximately 30 cubic centimeters.

The delay volume means 86 is heated by a delay volume furnace 88. The delay volume means is maintained at a temperature above 300° C., preferably 300°-350° C. by the delay volume furnace 88. The delay volume means 86 is heated to prevent any water vapor and sulfur trioxide gas present in the combustion gases from being converted to sulfuric acid.

The reduction chamber 94 is a tube, preferably a quartz tube, packed with granulated copper. Satisfactory results have been achieved using a tube packed with reduced copper wire, such as Cuprin, available from Coleman Instruments, Oak Brook, Ill.

The reduction chamber 94 is heated by a reduction chamber furnace 92. The reduction chamber 94 is maintained at a temperature above 800° C., preferably 800°-850° C., by the reduction furnace 92. The copper contained in the reduction chamber reduces the oxide of nitrogen to nitrogen, converts any sulfur trioxide present into sulfur dioxide and removes the unreacted oxygen. Conversion to nitrogen and sulfur dioxide and removal of the unreacted oxygen facilitates separation on the first chromatographic column 18 and subsequent detection. The reaction products mixture are then passed to first chromatographic column 18 for separation. The apparatus and method employed thereafter are the same as previously discussed with respect to the disclosure of FIG. 1.

FIG. 4 also shows the optional use of delay volume 186 with delay volume furnace 188 and reduction chamber 194 with reduction chamber furnace 192 in conduit means 184. The use and operation of these devices is identical to that described in FIG. 3.

In the combustion of organic or inorganic samples which contain sulfur, it has been discovered that metals or metal oxides present in the system, such as for example, tin, aluminum, barium, calcium, sodium and potassium react with the sulfur. When it is desired to detect for elemental sulfur, obviously these reactions are undesirable. By admixing vanadium pentoxide ($V_2O_5$) with the sample in an amount at least as great as the sample size, the reaction between sulfur and the metals or metal oxides is prevented. Satisfactory results have been achieved by admixing $V_2O_5$ with the sample in an amount two to ten times the size of said sample.

In this invention, many of the samples are encapsulated in tin sample containers and then the sample filled container is introduced into the combustion chamber. The use of vanadium pentoxide ($V_2O_5$) substantially prevents any trace metals present in the system, such as in the tin or aluminum in the sample containers, from reacting with the sulfur.

One advantage of the present invention is the saving of time as compared to the prior art methods. An analysis for carbonate carbon can be carried out according to the prevent invention in about one-third the time required heretofore.

Another advantage of the present invention is that slugging effects are eliminated or at least minimized. The first chromatographic column acts as a self-flushing trap for the troublesome and often copious combustion products, such as water, hydrogen chloride and the sulfur oxides. If these gases were not removed before measuring the carbon dioxide, they would cause serious slugging effects and increase the analysis time.

A further advantage of the present invention is that carbon-containing gases, such as carbon monoxide and methane, are separated on the nitrogen column and the carbon contents of these gases can be added to the carbon dioxide carbon content to obtain the true value for carbon on the sample.

A further understanding of the invention is obtained from a consideration of the following illustrative examples wherein a variety of samples were decomposed and analyzed in accordance with the apparatus and methods of this invention.

EXAMPLE I

A sample of hexane weight about 1.877 milligrams was analyzed in the apparatus essentially illustrated in FIG. 3, except that delay volume means and reduction chamber 94 were omitted. Sulfur dioxide gas permeation tubes 78, 80 and water vapor-emitting devices 76, 82 were positioned in the oxygen stream and carrier gas stream. The water vapor emitting devices normally should be upstream of the sulfur dioxide permeation tubes to prevent the formation of acid by the water and sulfur dioxide. Helium was employed as the first, second and third carrier gas. Ten cubic centimeters (cc.) of oxygen at 26 pounds pressure was introduced into a combustion chamber having a design essentially as illustrated in FIG. 7. The sample-containing tin capsule was introduced into the combustion chamber and was heated to a temperature of about 1050° C. Helium was admitted to the combustion chamber at the rate of 20 cc/minute and the combustion products were swept from the combustion chamber and introduced into a first chromatographic column packed with Carbowax. The first chromatographic column was maintained at a temperature of about 120° to 130° C. The second chromatographic column was packed with Porapak-Q and maintained at a temperature of 70° to 80° C. The third chromatographic column was packed with molecular sieve and maintained at a temperature of 70° to 80° C. All the detectors employed in this example were thermal conductivity cells connected to a recorder from which plots were obtained in the form of a chromatogram.

Figure 8:
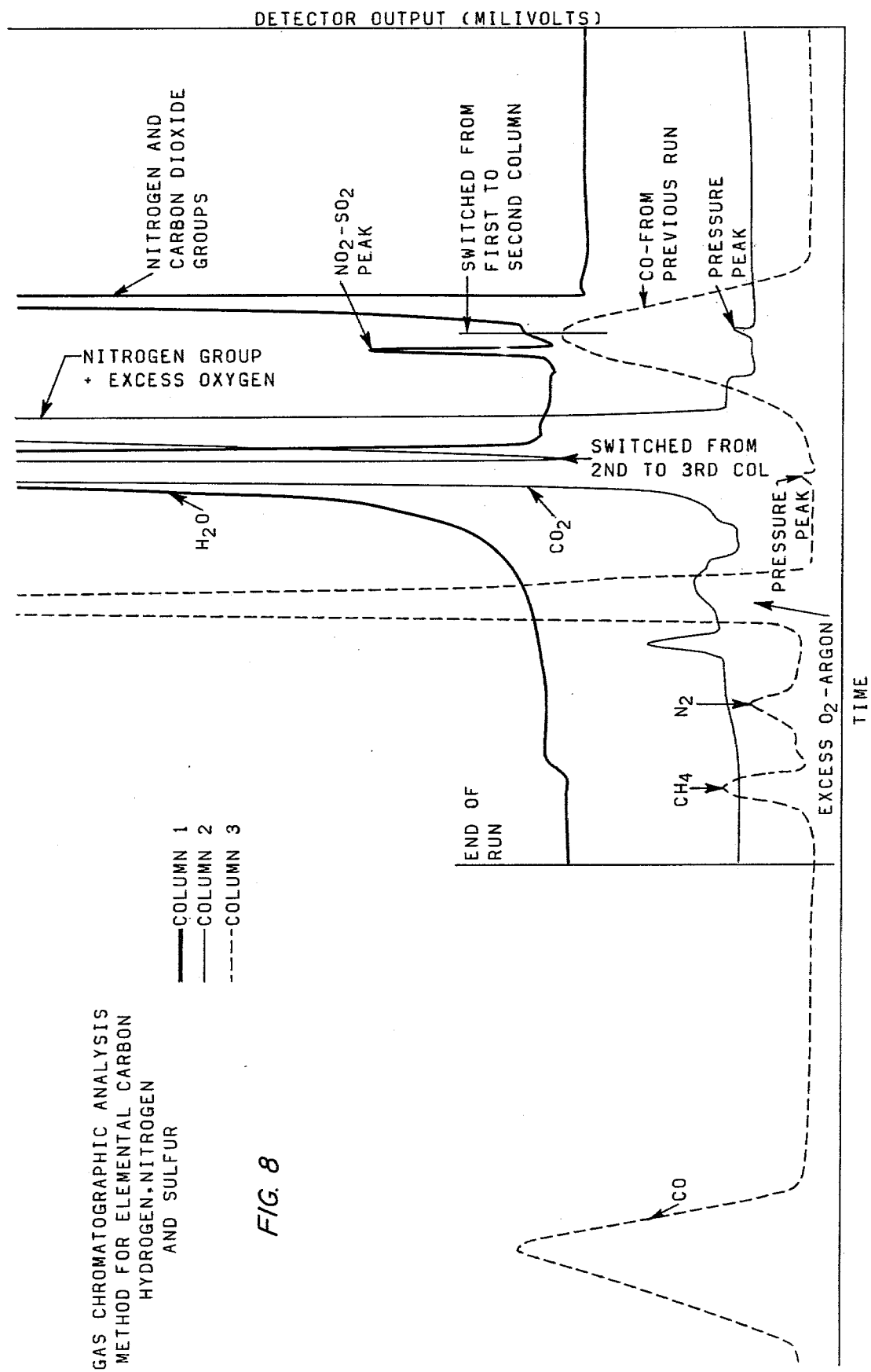
FIG. 8 is a chromatogram showing the products obtained by the oxidative decomposition of hexane.

FIG. 8 discloses the chromatogram of the products resulting from the oxidative decomposition of hexane. As illustrated in FIG. 8, on the first column, the nitrogen group gases elute prior to the water group gases (i.e., for example, water and sulfur dioxide). Although not shown in the first column, the carbon dioxide group also elutes prior to the water group. The carbon dioxide group and nitrogen group are passed to the second column wherein the carbon dioxide group is retained until the nitrogen group gases elute. As illustrated in FIG. 8, the carbon dioxide group (in this instance, carbon dioxide is the only major peak) is alone on its present optimized column after the nitrogen group gases have eluted. High measurement accuracy is obtained since any trace of contaminating peaks (such as the water group gases) are removed. The nitrogen group gases are passed to a third column wherein they are separated, as shown in FIG. 8, into carbon monoxide, oxygen, nitrogen, and methane. The third chromatographic column provides additional information with respect to whether other components are present in the nitrogen group peak on the first column. Previously, classical chromatography could not be reasonably sure that combustion of a sample was complete and therefore that the "nitrogen" peak contained only nitrogen. In an incomplete combustion of the sample, unconverted or partially converted products such as carbon monoxide and methane would appear together in the nitrogen peak giving a high and inaccurate value for nitrogen. Moreover, since the carbon monoxide and methane would appear undetected in the "nitrogen" peak, the carbon value in a sample would be low and inaccurate. Also, nitrogen as unreduced nitrogen oxides will not be in the nitrogen peak. FIG. 8 demonstrates that the partially converted or unconverted products can be separated on the third column. The carbon content of the carbon monoxide and methane are added to the carbon dioxide carbon content so as to give a true and accurate value for carbon in the sample. Furthermore, a true and accurate value for nitrogen is also obtained. Therefore, the completeness of combustion does not determine the accuracy of the analysis since the unconverted or partially converted products can be separated and detected on the third chromatographic column. Present conventional methods assume that a quantitative conversion has occurred to yield a single species for each element measured. This invention is able to make accurate quantitative determinations even though a complete quantitative conversion has not been obtained. Furthermore, the three groups of gases (water group, carbon dioxide group and nitrogen group) are concurrently separated and developed for measurement on their own optimized columns.

EXAMPLE II

A sample of sulfanilamide was analyzed in the apparatus illustrated in FIG. 4. The carrier gas, gas permeation tubes, column packings and apparatus temperatures were the same as described in Example I. The delay volume means was heated to 300° C. and the reduction chamber was heated to 825° C.

Figure 9:
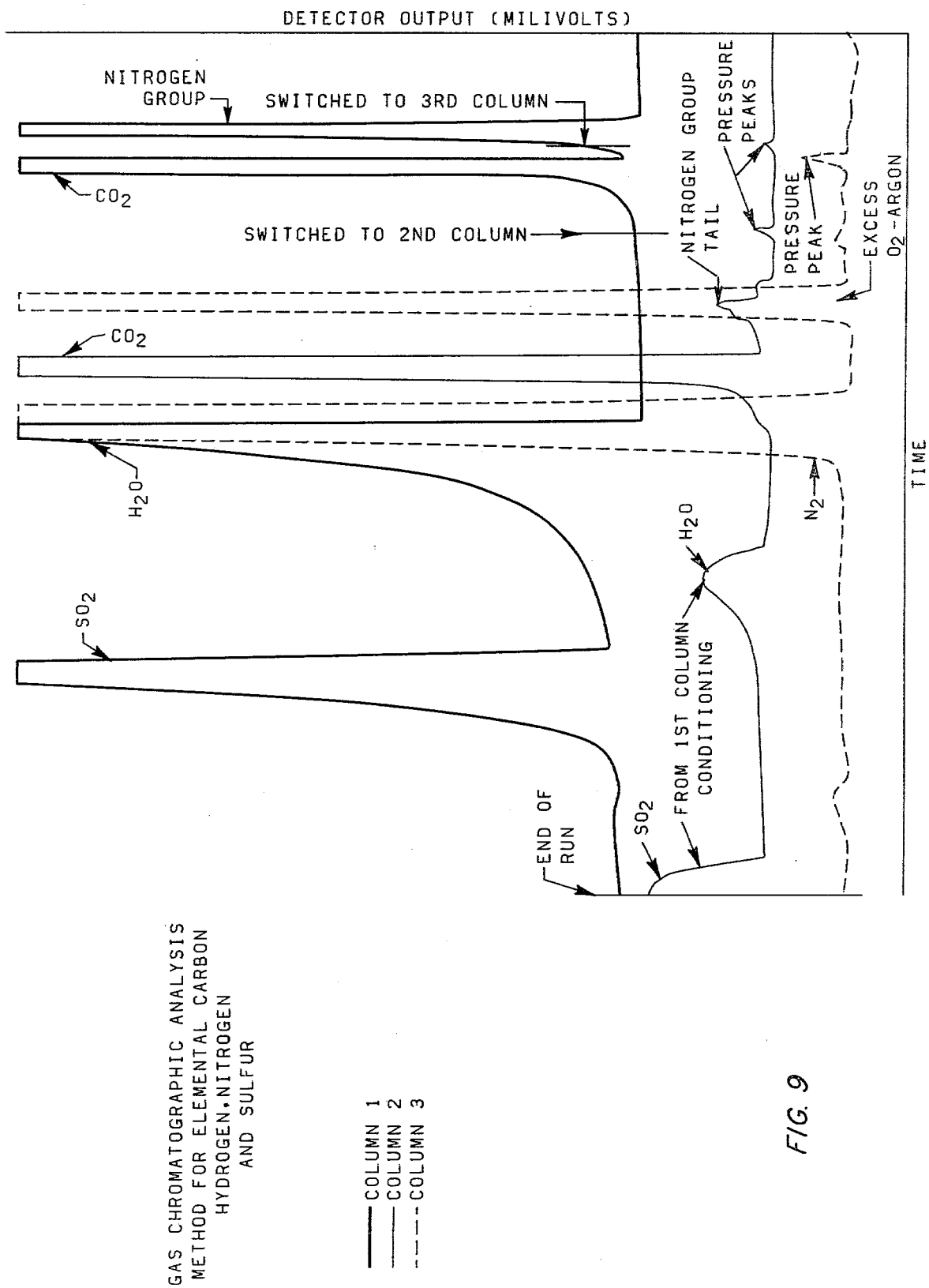
FIG. 9 is a chromatogram showing the products obtained by the oxidative decomposition of sulfanilamide.

FIG. 9 discloses the chromatogram of combustion products resulting from the oxidative decomposition of sulfanilamide. On the first column, the nitrogen group gases and carbon dioxide group gases eluted prior to the water group gases and the nitrogen group was passed to the third column. The carbon dioxide group was passed to the second column. Only carbon dioxide was found to be present in the CO₂ group. FIG. 9 demonstrates that a complete combustion was obtained in that no methane or carbon monoxide appeared in the third column. But, as previously stated, the operator of the apparatus is able to quantitatively determine and verify the components present in the nitrogen group whether or not a complete "burn" is obtained.

EXAMPLE III

Figure 10:
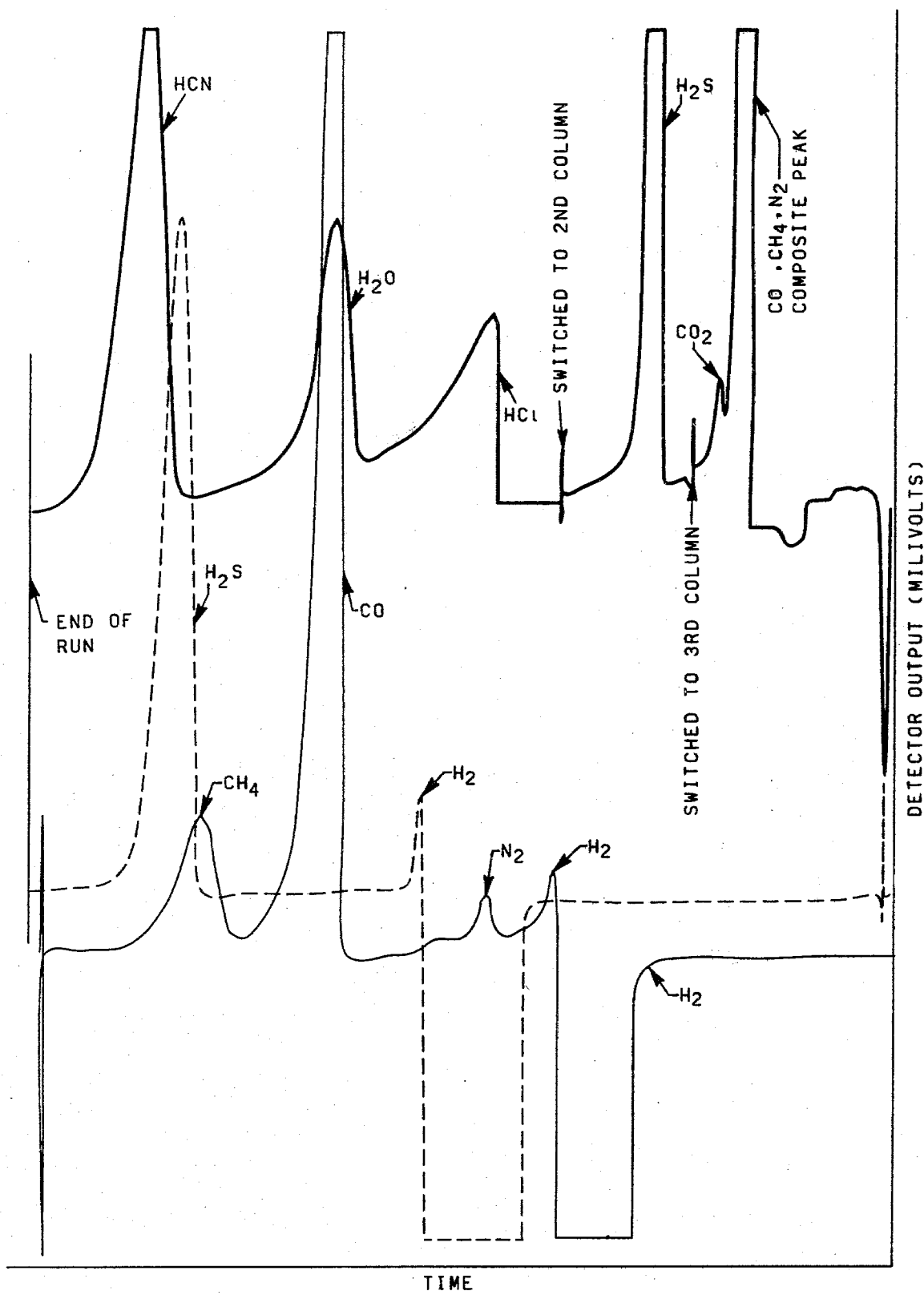
FIG. 10 is a chromatogram showing the products obtained by the pyrolytic decomposition of 8-quinolinesulfonyl chloride.

A sample of 8-quinolinesulfonyl chloride weighing about 3.779 milligrams was analyzed in the apparatus illustrated in FIG. 6. A hydrogen sulfide gas permeation tube was positioned in the hydrogen stream and carrier gas stream; a water vapor-emitting device was positioned after the pyrolysis chamber. Helium was employed as the second and third carrier gas. Hydrogen was employed as the first carrier gas and introduced into a pyrolysis chamber heated to 1120° C. The pyrolysis chamber contained graphite. Sample was dropped into the pyrolysis chamber and thereafter helium was introduced to sweep the pyrolysis products over the graphite. The products were swept into a first chromatographic column packed with Porapak-T; the column was maintained at a temperature of about 120° to 130° C. As illustrated in FIG. 10, when the light gas-such as nitrogen, methane, carbon monoxide, elute from the first column they are switched to the molecular sieve column (third column) for separation and measurement of the carbon monoxide. The third column was maintained at a temperature of about 70° to 80° C. Hydrogen sulfide was passed to a second column, packed with Porapak-Q and maintained at a temperature of about 70° to 80° C., for further separation and detection.

In previous methods for determining oxygen in organic compounds, the sample was pyrolyzed and the combustion products passed over hot carbon to convert all oxygen in the sample to carbon monoxide. The carbon monoxide could then be measured. However, in this method it was not possible to be reasonably sure that pyrolysis of the sample was complete and therefore that all the oxygen is present as carbon monoxide. In other methods, the carbon monoxide is converted to carbon dioxide using hot copper oxide. However, when measuring the carbon dioxide in this manner, interferences due to hydrogen sulfide, halogens, ammonia, cyanides and methane were encountered which gave unreliable results.

In the present invention, the carbon monoxide can be measured directly, without conversion to carbon dioxide, and interferences due to other gases are eliminated. Although not illustrated in FIG. 10, if the conversion of oxygen to carbon monoxide is incomplete ("a bad burn"), it will be evidenced by the presence of carbon dioxide and/or water peaks on the third column. However, since the present invention is able to adequately separate the CO from the $CO_2$ and $H_2O$ on the third column, the oxygen contents of the carbon dioxide and water peak may be added to the oxygen content of the carbon monoxide. Thus, use of the present invention enables the operator to determine the oxygen content of a sample even though there has been an incomplete conversion to carbon monoxide.

Reasonable variations and modifications, which will be apparent to those skilled in the art, can be made in this invention without departing from the spirit and scope thereof.

What is claimed is:

1. A gas chromatographic apparatus for determining at least the elemental carbon, hydrogen and nitrogen of a sample, which comprises:

a closed, heated combustion chamber,
means for introducing a sample into said chamber,
means for introducing a volume of oxygen gas into said chamber,
a first source of carrier gas,
means for introducing said first carrier gas into said chamber,
a first chromatographic column in communication with said chamber,
a first detector means in communication with said first column,
a second chromatographic column,
a second source of carrier gas,
first valve means, including first actuator means and first delay conduit means, in communication with said first detector means and connected to said second carrier gas source, for flowing the effluent from said first detector means through said first delay conduit means and for flowing said second carrier gas through a first conduit means to said second column when said first valve means is in the first position, and upon actuation of said first valve means wherein said first valve means is changed from the first position to the second position, for flowing said second carrier gas through said first delay conduit means and into said first conduit means thereby carrying at least a portion of the contents of said first delay conduit means into said second column,
a second detector means in communication with said second column,
a third chromatographic column,
a third source of carrier gas,
a second valve means, including a second actuator means and a second delay conduit means, in communication with said second detector means and connected to said third carrier gas source, for flowing the effluent from said second detector means through said second delay conduit means and for flowing said third carrier gas through a second conduit means to said third column when said second valve means is in the first position, and upon actuation of said second valve means wherein said second valve means is changed from the first position to the second position, for flowing said third carrier gas through said second delay conduit means and into said second conduit means thereby carrying at least a portion of the contents of said second delay conduit means into said third column, and
a third detector means in communication with said third column.

2. An apparatus according to claim 1 additionally having peak depressing means connected between said second column and said second detector means, said peak depressing means comprising a chamber having sufficient volume so related to the flow rate of said second carrier gas to allow mixing of said second carrier gas and the components of the gaseous mixture separated in said second column.

3. An apparatus according to claim 1 wherein said first valve means is a multiport valve means having a first, second, third, fourth, fifth and sixth ports and has first and second operating positions, including said first valve actuator means, with port one connected to port two, port three to port four and port five to port six when said first valve means is operating in said first position, and with port one connected to port six, port two to port three and port four to port five when said valve is in said second operating position, said first detector means being in communication with said port one, said first delay conduit means being connected between said port two and said port five, said second carrier gas source being in communication with said port three, said first conduit means being connected to said port four and a first discharge conduit means being connected to said port six.

4. An apparatus according to claim 1 wherein said second valve means is a multiport means having a first, second, third, fourth, fifth and sixth ports and has first and second operating positions, including said second valve actuator means, with port one connected to port two, port three to port four, and port five to port six when said second valve means is in said first operating position, and with port one connected to port six, port two to port three and port four to port five when said second valve means is in said second operating position, said second detector means being in communication with said port one, said second delay conduit means being connected between said port two and said port five, said third carrier gas source being in communication with said port three, said second conduit means being connected to said port four and a second discharge conduit means being connected to said port six.

5. An apparatus according to claim 1 further comprising timing means for sequentially actuating said sample introducing means, said oxygen introducing means, said first carrier gas introducing means, said first valve means and said second valve means.

6. An apparatus according to claim 1 further comprising flow stop valve means connected between said combustion chamber and said first column for interrupting the flow of gas therebetween for a period of time sufficient to ensure complete combustion of said sample in said chamber.

7. An apparatus according to claim 1 further comprising a means for introducing a conditioning gas into the first carrier gas being introduced into said heated combustion chamber and for introducing a conditioning gas into the oxygen being introduced into said heated combustion chamber.

8. An apparatus according to claim 7 wherein said means for introducing a conditioning gas into said carrier gas and said oxygen is a sulfur dioxide gas permeation tube.

9. An apparatus according to claim 8 further comprising means for introducing water vapor into said carrier gas and said oxygen prior to the introduction of sulfur dioxide therein.

10. An apparatus according to claim 7 wherein said conditioning gas is carbon tetrachloride gas and said means for introducing a conditioning gas into said carrier gas and oxygen is a carbon tetrachloride gas permeation tube.

11. An apparatus according to claim 1 further comprising a delay volume means and a reduction chamber positioned between said combustion chamber and said first chromatographic column wherein said reduction chamber is in communication with said delay volume means for preventing the entrance of excess oxygen into said reduction chamber until the combustion of the sample in said combustion chamber is substantially complete.

12. An apparatus according to claim 11 wherein said delay volume means has a volume at least as great as the volume of oxygen introduced into said combustion chamber and said reduction chamber contains copper particles.

13. An apparatus according to claim 1 wherein said heated combustion chamber comprises an elongated inlet means, a first heated combustion chamber, a second heated combustion chamber and an outlet means, in that order.

14. An apparatus according to claim 13 wherein said elongated inlet means is of sufficient length to preclude the condensation of oxidatively decomposed sample gases on the walls of the elongated inlet means when the apparatus is used for oxidatively decomposing a sample.

15. An apparatus according to claim 14 wherein a dampening chamber is positioned between and in communication with the second heated combustion chamber and the outlet means.

16. A gas chromatographic apparatus for determining at least the elemental carbon, hydrogen and nitrogen of a sample, which comprises:
   a closed, heated combustion chamber,
   means for introducing oxygen into said chamber,
   means for introducing a sample into said chamber,
   a first source of carrier gas,
   means for introducing said first carrier gas into said chamber,
   a first chromatographic column in communication with said chamber,
   a first detector means in communication with said first column,
   a second chromatographic column,
   a second source of carrier gas,
   a second detector means in communication with said second column,
   a third chromatographic column,
   a third source of carrier gas,
   a third detector means in communication with said third column,
   a first valve means, including first actuation means and first delay conduit means, in communication with said first detector means and connected to said second carrier gas source, for flowing the effluent from said first detector means through said first delay conduit means to a first conduit means and for flowing said second carrier gas through a second conduit means to said second column when said first valve means is in the first position, and upon actuation of said first valve means wherein said first valve means is changed from the first position to the second position, for flowing said second carrier gas through said first delay conduit means and into said second conduit means thereby carrying at least a portion of the contents of said first delay conduit means into said second column, and for directing the effluent from said first detector means through said first conduit means;
   a second valve means, including second actuator means and second delay conduit means, in communication with said first valve means through said first conduit and connected to said third carrier gas source, for flowing the effluent from said first conduit means through said second delay conduit means and for flowing said third carrier gas through a third conduit means to said third column when said second valve means is in the first position, and upon actuation of said second valve means wherein said second valve means is changed from the first position to the second position, for flowing said third carrier gas through said second delay conduit means and into said third conduit means thereby carrying at least a portion of the contents of said second delay conduit means into said third column.

17. An apparatus according to claim 16 additionally having peak depressing means connected between said second column and said second detector means, said peak depressing means comprising a chamber having sufficient volume so related to the flow rate of said second carrier gas to allow mixing of said second carrier gas and the components of the gaseous mixture separated in said second column.

18. An apparatus according to claim 16 wherein said first valve means is a multiport valve means having a first second, third, fourth, fifth and sixth ports and has first and second operating positions, including said first valve actuator means, with port one connected to port two, port three to port four and port five to port six when said first valve means is in said first operating position, and with port one connected to port six, port two to port three and port four to port five when said first valve means is in said second operating position, said first detector means being in communication with said port one, said first delay conduit means being connected between said port two and said port five, said second carrier gas source being in communication with said port three, said second conduit means being connected to said port four and said first conduit means being connected to said port six.

19. An apparatus according to claim 16 wherein said second valve means is a multiport means having first, second, third, fourth, fifth and sixth ports and has first and second operating positions, including said second valve actuator means, with port one connected to port two, port three to port four, and port five to port six when said second valve means is in said first operating position, and with port one connected to port six, port two to port three and port four to port five when said second valve means is in said second operating position, said first conduit means being connected to said port one, said second delay conduit means being connected between said port two and said port five, said third carrier gas source being in communication with said port three, said third conduit means being connected to said port four and a first discharge conduit means being connected to said port six.

20. An apparatus according to claim 16 further comprising timing means for sequentially actuating said sample introducing means, said oxygen introducing means, said first carrier gas introducing means, said first valve means and said second valve means.

21. An apparatus according to claim 16 further comprising flow stop valve means connected between said combustion chamber and said first column for interrupting the flow of gas therebetween for a period of time sufficient to ensure complete combustion of said sample in said chamber.

22. An apparatus according to claim 16 further comprising a means for introducing a conditioning gas into the carrier gas being introduced into said heated combustion chamber and for introducing a conditioning gas into the oxygen being introduced into said heated combustion chamber.

23. An apparatus according to claim 22 wherein said means for introducing a conditioning gas into said carrier gas and said oxygen is a sulfur dioxide gas permeation tube.

24. An apparatus according to claim 22 further comprising means for introducing water vapor into said carrier gas and said oxygen prior to the introduction of sulfur dioxide therein.

25. An apparatus according to claim 22 wherein said conditioning gas is carbon tetrachloride gas and said means for introducing a conditioning gas into said carrier gas and oxygen is a carbon tetrachloride gas permeation tube.

26. An apparatus according to claim 16 further comprising a delay volume means and a reduction chamber positioned between said combustion chamber and said first chromatographic column wherein said reduction chamber is in communication with said delay volume means for preventing the entrance of excess oxygen into said reduction chamber until the combustion of the sample in said combustion chamber is substantially complete.

27. An apparatus according to claim 26 wherein said delay volume means has a volume at least as great as the volume of oxygen introduced into said combustion chamber and said reduction chamber contains copper particles.

28. An apparatus according to claim 16 wherein said heated combustion chamber comprises an elongated inlet means, a first heated combustion chamber, a second heated combustion chamber and an outlet means, in that order.

29. An apparatus according to claim 28 wherein said elongated inlet means is of sufficient length to preclude the condensation of oxidatively decomposed sample gases on the walls of the elongated inlet means when the apparatus is used for oxidatively decomposing a sample.

30. An apparatus according to claim 28 wherein a dampening chamber is positioned between and in communication with the second heated combustion chamber and the outlet means.

31. A gas chromatographic apparatus for determining at least the elemental sulfur and oxygen of a sample, which comprises:
   a closed, heated pyrolysis chamber,
   means for introducing a sample into said pyrolysis chamber,
   a source of hydrogen gas,
   means for introducing hydrogen gas in to said pyrolysis chamber,
   a first source of carrier gas,
   means for introducing said first carrier gas into said pyrolysis chamber,
   a first chromatographic column in communication with said pyrolysis chamber,
   a first detector means in communication with said first column,
   a second chromatographic column,
   a second source of carrier gas,
   first valve means, including first actuator means and first delay conduit means, in communication with said first detector means and connected to said second carrier gas source, for flowing the effluent from said first detector means through said first delay conduit means and for flowing said second carrier gas through a first conduit means to said second column when said first valve means is in the first position, and upon actuation of said first valve means wherein said first valve means is changed from the first position to the second position, for flowing said second carrier gas through said first delay conduit means and into said first conduit means thereby carrying at least a portion of the contents of said first delay conduit means into said second column, and a second detector means in communication with said second column.

32. An apparatus according to claim 31 further comprising:
a third chromatographic column,
a third source of carrier gas,
a second valve means, including a second actuator means and a second delay conduit means, in communication with said second detector means and connected to said third carrier gas source, for flowing the effluent from said second detector means through said second delay conduit means and for flowing said third carrier gas through a second conduit means to said third column when said second valve means is in the first position, and upon actuation of said second valve means wherein said second valve means is changed from the first position to the second position, for flowing said third carrier gas through said second delay conduit means and into said second conduit means thereby carrying at least a portion of the contents of said second delay conduit means into said third column, and
a third detector means in communication with said third column.

33. An apparatus according to claim 31 additionally having peak depressing means connected between said second column and said second detector means, said peak depressing means comprising a chamber having sufficient volume so related to the flow rate of said second carrier gas to allow mixing of said second carrier gas and the components of the gaseous mixture separated in said second column.

34. An apparatus according to claim 31 wherein said first valve means is a multiport valve means having a first, second, third, fourth, fifth and sixth ports and has first and second operating positions, including said first valve actuator means, with port one connected to port two, port three to port four and port five to port six when said first valve means is in said first operating position, and with port one connected to port six, port two to port three and port four to port five when said valve is in said second operating position, said first detector means being in communication with said port one, said first delay conduit means being connected between said port two and said port five, said second carrier gas source being in communication with said port three, said first conduit means being connected to said port four and a first discharge conduit means being connected to said port six.

35. An apparatus according to claim 31 wherein said second valve means is a multiport means having first, second, third, fourth, fifth and sixth ports and has first and second operating positions, including said second valve actuator means, with port one connected to port two, port three to port four, and port five to port six when said second valve means is in said first operating position, and with port one connected to port six, port two to port three and port four to port five when said second valve means is in said second operating position, said second detector means being in communication with said port one, said second delay conduit means being connected between said port two and said port five, said third carrier gas source being in communication with said port three, said second conduit means being connected to said port four and a second discharge conduit means being connected to said port six.

36. An apparatus according to claim 31 further comprising timing means for sequentially actuating said sample introducing means, said hydrogen introducing means said first carrier gas introducing means, said first valve means and said second valve means.

37. An apparatus according to claim 31 further comprising flow stop valve means connected between said combustion chamber and said first column for interrupting the flow of gas therebetween for a period of time sufficient to ensure complete pyrolysis of said sample in said chamber.

38. The apparatus of claim 31 wherein said first carrier gas is hydrogen and said means for introducing hydrogen into said pyrolysis chamber is said means for introducing said carrier gas into said pyrolysis chamber.

39. An apparatus according to claim 31 further comprising a means for introducing a conditioning gas into the first carrier gas being introduced into said heated pyrolysis chamber and for introducing a conditioning gas into the hydrogen being introduced into said heated pyrolysis chamber.

40. An apparatus according to claim 39 wherein said conditioning gas is hydrogen sulfide gas and said means for introducing a conditioning gas into said carrier gas and said hydrogen is a hydrogen sulfide gas permeation tube.

41. An apparatus according to claim 40 further comprising means for introducing water vapor into the gas passed to the first chromatographic column from the pyrolysis chamber.

42. An apparatus according to claim 39 wherein said conditioning gas is carbon tetrachloride gas and said means for introducing a conditioning gas into said carrier gas and hydrogen is a carbon tetrachloride gas permeation tube.

43. A gas chromatographic apparatus for determining at least the elemental sulfur and oxygen of a sample, which comprises:
a close, heated pyrolysis chamber,
means for introducing a sample into said pyrolysis chamber,
a source of hydrogen gas,
a first source of carrier gas,
means for introducing hydrogen gas into said pyrolysis chamber,
means for introducing said first carrier gas into said pyrolysis chamber,
a first chromatographic column in communication with said pyrolysis chamber,
a first detector means in communication with said first column,
a second chromatographic column,
a second source of carrier gas,
a second detector means in communication with said second column,
a third chromatographic column,
a third source of carrier gas,
a third detector means in communication with said third column,
a first valve means, including first actuation means and first delay conduit means, in communication with said first detector means and connected to said second carrier gas source, for flowing the effluent from said first detector means through said first delay conduit means to a first conduit means and for flowing said second carrier gas through a second conduit means to said second column when said first valve means is in the first position, and upon actuation of said first valve means wherein said first valve means is changed from the first position to the second position, for flowing said second carrier gas through said first delay conduit means and into said second conduit means thereby carrying at least a portion of the contents of said first delay conduit means into said second column, and for directing the effluent from said first detector means through said first conduit means;

a second valve means, including second actuator means and second delay conduit means, in communication with said first valve means through said first conduit and connected to said third carrier gas source, for flowing the effluent from said first conduit means through said second delay conduit means and for flowing said third carrier gas through a third conduit means to said third column when said second valve means is in the first position, and upon actuation of said second valve means wherein said second valve means is changed from the first position to the second position, for flowing said third carrier gas through said second delay conduit means and into said third conduit means thereby carrying at least a portion of the contents of said second delay conduit means into said third column.

44. An apparatus according to claim 43 additionally having peak depressing means connected between said second column and said second detector means, said peak depressing means comprising a chamber having sufficient volume so related to the flow rate of said second carrier gas to allow mixing of said second carrier gas and the components of the gaseous mixture separated in said second column.

45. An apparatus according to claim 43 wherein said first valve means is a multiport valve means having first, second, third, fourth, fifth and sixth ports and has first and second operating positions, including said first valve actuator means, with port one connected to port two, port three to port four and port five to port six when said first valve means is in said first operating position, and with port one connected to port six, port two to port three and port four to port five when said first valve means is in said second generating position, said first detector means being in communication with said port one, said first delay conduit means being connected between said port two and said port five, said second carrier gas source being in communication with said port three, said second conduit means being connected to said port four and said first conduit means being connected to said port six.

46. An apparatus according to claim 43 wherein said second valve means is a multiport means having first, second, third, fourth, fifth and sixth ports and has first and second operating positions, including said second valve actuator means, with port one connected to port two, port three to port four, and port five to port six when said second valve means is in said first operating position, and with port one connected to port six, port two to port three and port four to port five when said second valve means is in said second operating position, said first conduit means being connected to said port one, said second delay conduit means being connected between said port two and said port five, said third carrier gas source being in communication with said port three, said third conduit means being connected to said port four and a first discharge conduit means being connected to said port six.

47. An apparatus according to claim 43 further comprising timing means for sequentially actuating said sample introducing means, said hydrogen introducing means, said first carrier gas introducing means, said first valve means and said second valve means.

48. An apparatus according to claim 43 further comprising flow stop valve means connected between said combustion chamber and said first column for interrupting the flow of gas therebetween for a period of time sufficient to ensure complete pyrolysis of said sample in said chamber.

49. An apparatus according to claim 43 wherein said first carrier gas is hydrogen and said means for introducing hydrogen into said pyrolysis chamber is said means for introducing said carrier gas into said pyrolysis chamber.

50. An apparatus according to claim 43 further comprising a means for introducing a conditioning gas into the first carrier gas being introduced into said heated pyrolysis chamber and for introducing a conditioning gas into the hydrogen being introduced into said heated pyrolysis chamber.

51. An apparatus according to claim 50 wherein said conditioning gas is hydrogen sulfide gas and said means for introducing a conditioning gas into said carrier gas and said hydrogen is a hydrogen sulfide gas permeation tube.

52. An apparatus according to claim 51 further comprising means for introducing water vapor into the gas passed to the first chromatographic column from the pyrolysis chamber.

53. An apparatus according to claim 50 wherein said conditioning gas is carbon tetrachloride gas and said means for introducing a conditioning gas into said carrier gas and hydrogen is a carbon tetrachloride gas permeation tube.

54. An apparatus comprising:
an elongated conduit suitable for passing a substance therethrough, said conduit having an elongated inlet means, a first chamber, a second chamber and an outlet means in that order.

55. An apparatus according to claim 54 wherein said elongated inlet means is of sufficient length to preclude the condensation of oxidatively decomposed sample gases on the walls thereof when the apparatus is used for oxidatively decomposing a sample in a gas chromatographic analyzer.

56. An apparatus according to claim 54 wherein at least a portion of said first chamber contains an inert packing positioned near said second chamber.

57. An apparatus according to claim 56 wherein said inert packing has a melting point of at least 1200° C.

58. An apparatus according to claim 57 wherein said inert packing is quartz wool.

59. An apparatus according to claim 56 wherein said inert packing supports at least one inert subdivided substance wherein said inert subdivided substance has a melting point of at least 1200° C.

60. An apparatus according to claim 59 wherein said at least one inert subdivided substance has a particle size in the range of about 40 mesh to about ¼ inch diameter.

61. An apparatus according to claim 60 wherein said at least one inert subdivided substance is a quartz chip.

62. An apparatus according to claim 54 wherein a dampening chamber is positioned between and is in communication with said second chamber and said outlet means.

63. An apparatus according to claim 62 wherein at least a portion of said dampening chamber contains an inert packing.

64. An apparatus according to claim 63 wherein said inert packing has a melting point of at least 1200° C.

65. An apparatus according to claim 63 wherein said inert packing is quartz wool.

66. An apparatus according to claim 62 wherein said dampening chamber is substantially filled with quartz wool.

67. An apparatus according to claim 54 wherein said elongated conduit is constructed of quartz glass.

68. An apparatus according to claim 54 wherein said first chamber is partially formed by an inert packing and wherein said inert packing forms a portion of said second chamber.

69. An apparatus comprising:
an elongated conduit suitable for passing a substance therethrough, said conduit having an elongated inlet means, a first chamber, a second chamber and an outlet means in that order,
wherein said elongated inlet means is of sufficient length to preclude the condensation of a combustion gas on the walls thereof when the apparatus is used for oxidatively decomposing a sample in a chromatographic analyzer,
wherein said first chamber and said second chamber are partially formed by quartz wool packing having a melting point of at least 1200° C.,
wherein said inlet chamber has a volume within a range of about 20 to about 50 cubic centimeters and said second chamber has a volume within a range of about 5 to about 10 cubic centimeters,
wherein said quartz wool packing supports at least one quartz chip having a ⅛ inch diameter and a melting point of at least 1200° C.,
wherein a dampening chamber is positioned between and in communication with said second chamber and said outlet means,
wherein said dampening chamber is substantially filled with quartz wool packing having a melting point of at least 1200° C., and
wherein said elongated conduit is constructed of quartz glass.

70. A method for determining at least the elemental carbon, hydrogen and nitrogen content of a sample which comprises in combination, the steps of:
a. introducing an oxygen source into a closed, heated combustion chamber,
b. introducing a measured sample into said chamber,
c. oxidatively decomposing said sample whereby the resulting reaction product mixture contains as its principal components a carbon dioxide group, a water group and a nitrogen group,
d. retaining said reaction product mixture in said chamber until combustion of the sample is substantially complete,
e. sweeping substantially all of the reaction product mixture from said chamber with a first inert carrier gas at a predetermined flow rate,
f. passing said reaction product mixture and said inert gas through a first gas chromatographic column whereby said mixture is separated into said carbon dioxide group, said nitrogen group and said water group, said carbon dioxide group and said nitrogen group being eluted substantially simultaneously and prior to said water group,
g. passing the water group effluent eluting from said first column through a first detecting means to detect the quantity of water in said water group,
h. passing the carbon dioxide group and the nitrogen group effluent eluting from said first detecting means to a second gas chromatographic column,
i. introducing a second carrier gas at a predetermined flow rate to the inlet of said second column thereby passing said carbon dioxide group and said nitrogen group through said second column whereby said nitrogen group and said carbon dioxide group are further separated,
j. venting said water group eluting from said first detecting means,
k. passing the effluent from said second chromatographic column through a second detecting means to detect the quantities of carbon dioxide in said carbon dioxide group and nitrogen in said nitrogen group, and
l. separately determining from the quantity of said water, said carbon dioxide and said nitrogen the quantities of elemental hydrogen, carbon and nitrogen of said sample.

71. A method according to claim 70 further comprising the steps of:
a. passing said nitrogen group eluting from said second detecting means to a third chromatographic column,
b. introducing a third carrier gas at a predetermined flow rate to the inlet of said third column thereby sweeping said nitrogen group through said third column,
c. venting said carbon dioxide group eluting from said second detecting means, and
d. passing the effluent from said third chromatographic column through a third detecting means.

72. A method according to claim 70 further comprising the step of passing said effluent from said second chromatographic column through a serially connected carbon dioxide peak depressor, said depressor being a chamber having sufficient volume so related to the flow of said second carrier gas to allow mixing of said second carrier gas and said effluent from said second chromatographic column.

73. A method according to claim 71 further comprising the step of passing said effluent from said second chromatographic column through a serially connected carbon dioxide peak depressor, said depressor being a chamber having sufficient volume so related to the flow of said second carrier gas to allow mixing of said second carrier gas and said effluent from said second chromatographic column.

74. A method according to claim 70 further comprising passing said nitrogen group and said carbon dioxide group effluent from said first detector means through a first delay conduit means, said first delay conduit means having a sufficient volume so related to said predetermined flow rate as to delay in time said nitrogen group and carbon dioxide group and to prevent said water group from passing to said second column.

75. A method according to claim 71 further comprising passing said nitrogen group and said carbon dioxide group effluent from said first detector means through a first delay conduit means, said first delay conduit means having a sufficient volume so related to said predetermined flow rate as to delay in time said nitrogen group and carbon dioxide group and to prevent said water group from passing to said second column, and passing the nitrogen group effluent from said second detector through a second delay conduit means, said second delay conduit means having a sufficient volume so related to said predetermined flow rate as to delay in time said nitrogen group and to prevent said carbon dioxide group from passing to said third column.

76. A method according to claim 70 wherein, prior to step (a), said sample is decarbonated by a wet acid treatment with hydrochloric acid or by treatment with hydrogen chloride vapor.

77. A method according to claim 76 wherein said wet acid treatment comprises contacting said sample with a hydrochloric acid solution having a concentration in the range of 32 to 34 percent.

78. A method according to claim 76 wherein said treatment with hydrogen chloride vapor comprises contacting said sample with water vapor and thereafter surrounding said sample with hydrogen chloride vapor under pressure.

79. A method according to claim 70 wherein elemental sulfur is additionally determined from the quantity of sulfur oxides present in said water group.

80. A method according to claim 70 wherein elemental chlorine is additionally determined from the quantity of $Cl_2$ and hydrogen chloride in said water group.

81. A method according to claim 70 wherein said oxygen source and said first inert carrier gas when introduced into said combustion chamber contains at least one conditioning gas wherein said conditioning gas is selected from the group consisting of a sulfur dioxide conditioning gas introduced into said oxygen source and said first inert carrier gas by a sulfur dioxide gas permeation tube, a carbon tetrachloride conditioning gas introduced into said oxygen source and said first inert carrier gas by a carbon tetrachloride gas permeation tube and a water vapor conditioning gas introduced into said oxygen source and said first inert carrier gas by a water vapor emitting vessel.

82. A method according to claim 70 further comprising passing said reaction product mixture and said first inert carrier gas from said chamber through a heated delay volume means and into a heated reduction chamber containing copper.

83. A method according to claim 70 wherein said heated combustion chamber comprises a first combustion zone and a second combustion zone, wherein said sample is introduced into said first combustion zone to produce sample gases which are at least partially oxidatively decomposed therein and the sample gases in the first combustion zone are passed to the second combustion zone by passing the inert carrier gas into the first combustion zone said sample gases being passed to said second combustion zone to ensure essentially complete oxidative decomposition of the sample gases and to produce the reaction product mixture which is passed to the first gas chromatographic column.

84. A method according to claim 83 wherein the reaction product mixture is passed from the second combustion zone to the first chromatographic column through a dampening zone.

85. A method according to claim 70 wherein said measured sample, prior to introduction into said chamber, is admixed with vanadium pentoxide in an amount at least as great as the sample size.

86. A method according to claim 85 wherein said vanadium pentoxide is admixed with said sample in an amount two to ten times the size of said sample.

87. A method according to claim 86 wherein said vanadium pentoxide containing admixture is encapsulated in a tin sample container.

88. A method for determining at least the elemental carbon, hydrogen and nitrogen content of a sample which comprises in combination, the steps of:
 a. introducing an oxygen source into a closed, heated combustion chamber,
 b. introducing a measured sample into said chamber,
 c. oxidatively decomposing said sample whereby the resulting reaction product mixture contains as its principal components a water group, carbon dioxide group and nitrogen group,
 d. retaining said reaction product mixture in said chamber until combustion of said sample is substantially complete,
 e. sweeping substantially all of the reaction product mixture from said chamber with a first carrier gas at a predetermined flow rate,
 f. passing said reaction product mixture and said carrier gas through a first gas chromatographic column whereby said mixture is separated into said carbon dioxide group, said nitrogen group and said water group, said carbon dioxide group and said nitrogen group being eluted prior to said water group,
 g. passing the water group effluent from said first column through a first detecting means to detect the quantity of water in said water group,
 h. passing said nitrogen group effluent eluting from said first detecting means to a second gas chromatographic column,
 i. introducing a second carrier gas at a predetermined flow rate to the inlet of said second column thereby sweeping said nitrogen group through said column,
 j. passing said carbon dioxide group effluent eluting from said first chromatographic column to a third chromatographic column,
 k. introducing a third carrier gas at a predetermined flow rate to the inlet of said third column thereby sweeping said carbon dioxide group through said column,
 l. venting said water group eluting from said first detecting means,
 m. passing the effluent from said second column through a second detecting means to detect the quantity of nitrogen in said nitrogen group,
 n. passing the effluent from said third column through a third detecting means to detect the quantity of carbon dioxide in said carbon dioxide group, and
 o. separately determining from the quantity of said water, said carbon dioxide and said nitrogen the quantities of elemental hydrogen, carbon and nitrogen of said sample.

89. A method according to claim 88 further comprising the step of passing said effluent from said second chromatographic column through a serially connected carbon dioxide peak depressor, said depressor being a chamber having sufficient volume so related to the flow of said second carrier gas to allow mixing of said second carrier gas and said effluent from said second chromatographic column.

90. A method according to claim 88 wherein elemental sulfur is additionally determined from the quantity of sulfur oxides in said water group.

91. A method according to claim 88 wherein, prior to step (a), said sample is decarbonated by a wet acid treatment with hydrochloric acid or by treatment with hydrogen chloride vapor.

92. A method according to claim 91 wherein said wet acid treatment comprises contacting said sample with water vapor and thereafter allowing said sample to stand over a hydrochloric acid solution having a concentration in the range of 32 to 34 percent.

93. A method according to claim 91 wherein said treatment with hydrogen chloride vapor comprises contacting said sample with water vapor and thereafter surrounding said sample with hydrogen chloride vapor under pressure.

94. A method according to claim 88 wherein elemental chlorine is additionally determined from the quantity of $Cl_2$ and hydrogen chloride in said water group.

95. A method according to claim 88 wherein said oxygen source and said first inert carrier gas when introduced into said combustion chamber contains at least one conditioning gas wherein said conditioning gas is selected from the group consisting of a sulfur dioxide conditioning gas introduced into said oxygen source and said first inert carrier gas by a sulfur dioxide gas permeation tube, a carbon tetrachloride conditioning gas introduced into said oxygen source and said first inert carrier gas by a carbon tetrachloride gas permeation tube and a water vapor conditioning gas introduced into said oxygen source and said first inert carrier gas by a water vapor-emitting vessel.

96. A method according to claim 88 further comprising passing said reaction product mixture and said first inert carrier gas from said chamber through a heated delay volume means and into a heated reduction chamber containing copper.

97. A method according to claim 88 wherein said heated combustion chamber comprises a first combustion zone and a second combustion zone, wherein said sample is introduced into said first combustion zone to produce sample gases which are at least partially oxidatively decomposed therein and the sample gases in the first combustion zone are passed to the second combustion zone by passing the inert carrier gas into the first combustion zone said sample gases being passed to said second combustion zone to ensure essentially complete oxidative decomposition of the sample gases and to produce the reaction product mixture which is passed to the first gas chromatographic column.

98. A method according to claim 97 wherein the reaction product mixture is passed from the second combustion zone to the first chromatographic column through a dampening zone.

99. A method according to claim 88 wherein said measured sample, prior to introduction into said chamber, is admixed with vanadium pentoxide in an amount at least as great as the sample size.

100. A method according to claim 99 wherein said vanadium pentoxide is admixed with said sample in an amount two to ten times the size of said sample.

101. A method according to claim 100 wherein said vanadium pentoxide containing admixture is encapsulated in a tin sample container.

102. A method for determining at least the elemental oxygen content of a sample which comprises, in combination, the steps of:
 a. introducing a measured sample into a closed, heated pyrolysis chamber,
 b. pyrolytically decomposing said sample whereby the resulting reaction product mixture comprises water, carbon dioxide and carbon monoxide,
 c. retaining said reaction product mixture in said chamber until pyrolysis of said sample is substantially complete,
 d. sweeping substantially all of the reaction product mixture with a first carrier gas at a predetermined rate through a bed of carbon thereby converting at least a portion of said carbon dioxide to carbon monoxide and at least a portion of said water to carbon monoxide and hydrogen and thereafter passing the resulting product mixture and said carrier gas through a first gas chromatographic column whereby said mixture is separated into said carbon monoxide, said carbon dioxide, and said water, said carbon monoxide and said carbon dioxide being eluted prior to said water,
 e. passing the effluent from said first column through a first detecting means to detect the quantity of said water,
 f. passing said carbon monoxide and said carbon dioxide eluting from said first detecting means to a second gas chromatographic column,
 g. introducing a second carrier gas at a predetermined flow rate to the inlet of said second column thereby passing said carbon monoxide and said carbon dioxide through said second column whereby said carbon monoxide and said carbon dioxide are further separated,
 h. venting said water eluting from said first detecting means,
 i. passing the effluent from said second chromatographic column through a second detecting means to detect the quantities of said carbon dioxide and said carbon monoxide, and
 j. determining from the quantity of water, carbon dioxide and carbon monoxide the quantity of elemental oxygen of said sample.

103. A method according to claim 102 further comprising passing said effluent from said first detector means through a first delay conduit means, said first delay conduit means having a sufficient volume so related to said predetermined flow rate to delay in time said water component to prevent said water from passing to said second column.

104. A method according to claim 102 wherein said carbon is carbon black.

105. A method according to claim 102 wherein said carbon is graphite.

106. A method according to claim 102 further comprising passing said reaction product through platinum gauze.

107. A method for determining at least the elemental sulfur and oxygen content of a sample which comprises, in combination, the steps of:
 a. introducing a measured sample into a closed, heated pyrolysis chamber,
 b. pyrolytically decomposing said sample whereby the reaction product mixture comprises carbon monoxide, carbon dioxide, water and sulfur oxides,
 c. retaining said reaction product mixture in said chamber until pyrolysis of said sample is substantially complete,
 d. sweeping substantially all of the reaction product mixture with a first inert carrier gas at a predetermined rate through a bed of carbon, thereby converting at least a portion of said carbon dioxide to carbon monoxide, at least a portion of said water to carbon monoxide and hydrogen, and at least a portion of said sulfur oxides together with hydrogen to carbon monoxide and hydrogen sulfide, and thereafter passing the resulting product mixture and said first carrier gas through a first gas chromatographic column whereby said mixture is separated into said carbon monoxide, said hydrogen sulfide and said water, said carbon monoxide being eluted prior to said hydrogen sulfide which is prior to said water, e. passing the effluent from said first column through a first detecting means to detect the quantity of said water and said hydrogen sulfide, f. passing said carbon monoxide eluting from said first detecting means to a second gas chromatographic column, g. introducing a second carrier gas at a predetermined flow rate to the inlet of said second column thereby passing said carbon monoxide through said second column, h. venting said water and said hydrogen sulfide eluting from said first detecting means, i. passing the effluent from said second column through a second detecting means to detect the quantity of said carbon monoxide, and j. determining from the quantity of water, carbon monoxide and hydrogen sulfide the quantity of elemental oxygen and elemental sulfur of said sample.

108. The method of claim 107 wherein said carbon bed is graphite.

109. The method of claim 107 wherein said carbon bed is carbon black.

110. The method of claim 107 wherein said first carrier gas is hydrogen.

111. The method of claim 107 wherein prior to step (a) hydrogen is introduced into said closed, heated pyrolysis chamber.

112. The method of claim 111 wherein said hydrogen and said first inert carrier gas introduced into the pyrolysis chamber contain at least one conditioning gas wherein said conditioning gas is selected from the group consisting of a hydrogen sulfide conditioning gas introduced into said hydrogen and said first inert carrier gas by a hydrogen sulfide gas permeation tube and a chlorine-containing conditioning gas introduced into said hydrogen and said first inert carrier gas by a chlorine-emitting gas permeation tube.

113. The method of claim 112 wherein said chlorine-containing conditioning gas is carbon tetrachloride and said chlorine-emitting gas permeation tube is a carbon tetrachloride gas permeation tube.

114. A method according to claim 113 wherein water vapor is added to the product mixture which is passed from the pyrolysis chamber to the first gas chromatographic column.

115. A method for oxidatively decomposing a sample which comprises, in combination, the steps of:

a. passing oxygen into a first heated combustion zone and a second heated combustion zone to substantially fill each zone with oxygen, b. passing a sample into said first heated combustion zone wherein said sample is converted to gases which are at least partially oxidatively decomposed in the first heated combustion zone, c. passing an inert carrier gas into said first heated combustion zone to sweep the gases therein into said second heated combustion zone to ensure essentially complete oxidative decomposition of said sample gases, and d. passing said oxidatively decomposed sample gases through an outlet zone.

116. A method according to claim 115 further comprising passing said oxidatively decomposed sample gases from said second combustion zone through a dampening zone prior to passing said oxidatively decomposed sample gases through said outlet zone.

* * * * *

UNITED STATES PATENT AND TRADEMARK OFFICE
CERTIFICATE OF CORRECTION

PATENT NO. : 4,234,315
DATED : November 18, 1980
INVENTOR(S) : Richard L. Scott

It is certified that error appears in the above-identified patent and that said Letters Patent are hereby corrected as shown below:

Column 23, line 57, after "the" insert --- first ---;
Column 27, line 44, delete "generating" and substitute --- operating ---.

Signed and Sealed this

Twenty-first Day of July 1981

[SEAL]

Attest:

GERALD J. MOSSINGHOFF

*Attesting Officer*  *Commissioner of Patents and Trademarks*